US008212046B2

(12) United States Patent
Hashimoto et al.

(10) Patent No.: US 8,212,046 B2
(45) Date of Patent: *Jul. 3, 2012

(54) PROCESS FOR PRODUCING CRYSTAL

(75) Inventors: Hideo Hashimoto, Hyogo (JP); Hideaki Maruyama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/168,121

(22) Filed: Jun. 24, 2011

(65) Prior Publication Data

US 2011/0257405 A1 Oct. 20, 2011

Related U.S. Application Data

(62) Division of application No. 12/492,735, filed on Jun. 26, 2009, now Pat. No. 7,994,332, which is a division of application No. 11/515,639, filed on Sep. 5, 2006, now Pat. No. 7,569,696, which is a division of application No. 10/275,334, filed as application No. PCT/JP01/04014 on May 15, 2001, now Pat. No. 7,169,799.

(30) Foreign Application Priority Data

May 15, 2000 (JP) .................................. 2000-141670

(51) Int. Cl.
C07D 401/00 (2006.01)
(52) U.S. Cl. .................................................. 546/273.4
(58) Field of Classification Search ................ 546/273.4
See application file for complete search history.

(56) References Cited

U.S. PATENT DOCUMENTS

| 4,628,098 A | 12/1986 | Nohara |
| 6,002,011 A | 12/1999 | Kato et al. |
| 6,462,058 B1 | 10/2002 | Fujishima et al. |
| 6,664,276 B2 | 12/2003 | Fujishima et al. |
| 7,169,799 B2 | 1/2007 | Hashimoto et al. |
| 7,569,696 B2 * | 8/2009 | Hashimoto et al. ........ 546/273.4 |
| 2007/0265335 A1 | 11/2007 | Liu et al. |

FOREIGN PATENT DOCUMENTS

| CN | 1223262 | 7/1999 |
| EP | 0 302 720 | 2/1989 |
| EP | 0 174 726 | 3/1996 |
| EP | 1 191 025 | 3/2002 |
| WO | 92/08716 | 5/1992 |
| WO | 96/02535 | 2/1996 |
| WO | 96/17077 | 6/1996 |
| WO | 97/02261 | 1/1997 |
| WO | 98/21201 | 5/1998 |
| WO | 98/28294 | 7/1998 |
| WO | 99/38512 | 8/1999 |
| WO | 99/38513 | 8/1999 |
| WO | 00/78745 | 12/2000 |
| WO | 02/44167 | 6/2002 |

OTHER PUBLICATIONS

Concise Encyclopedia Chemistry, Translated and revised by Mary Eagleson (1994), Walter de Gruyter: New York, pp. 872 and 87.
Rouhi, A. Maureen, "The Right Stuff", C & E News (Feb. 24, 2003), pp. 32-35.
Curin, A. Sitar, "Study of Crystal Modifications of Lansoprazole using FT-IR . . . " The Second Central European Symposium on Pharmaceutical Technology (1997), pp. 290-291.
Vrecer, F. et al., "Study of Influence of Temperature and Griding on the . . . " The Second Central European Symposium on Pharmaceutical Technology (1997), pp. 242 and 243.
Katsuki, H. et al., "Determination of R(+)- and S(−)- Lansoprazole Using Chiral Stationalry-Phase Liquid . . . ", Pharmaceutical Research, vol. 13, No. 4, (1996), pp. 611-615.
Nagaya, H., et al., "Effects of the Enantiomers of Lansoprazole (AG-1749) . . . ", Biochemical Pharmacology, vol. 42, No. 10 (1991), pp. 1875-1878.
"Experimental Chemistry: Organic Reactions", JP Document and English Translation, vol. 18, published May 23, 1957.
Borner, et al., "Separation of Lansoprazole Enantiomers in Human Serum by HPLC", Chromatographia vol. 47, No. 3/4, Feb. 1998, pp. 171-175.
Arimori, et al., "Pharmacokinetic Differences Between Lansoprazole Enantiomers in Rats", J. Pharm. Pharmacol., vol. 50, No. 11, 1998, pp. 1241-1245.

* cited by examiner

*Primary Examiner* — Nizal Chandrakumar
(74) *Attorney, Agent, or Firm* — Hamre, Schumann, Mueller & Larson, P.C.

(57) ABSTRACT

The present invention relates to a production method of a crystal of (R)-2-[[[3-methyl-4-(2,2,2-trifluoroethoxy)-2-pyridyl]methyl]sulfinyl]benzimidazole.n'$H_2O$ (wherein n' is about 0 to about 0.1) or a salt thereof, which characteristically includes crystallization from an organic solvent solution or suspension in which (R)-2-[[[3-methyl-4-(2,2,2-trifluoroethoxy)-2-pyridyl]methyl]sulfinyl]benzimidazole.n$H_2O$ (wherein n is about 0.1 to about 1.0) or a salt thereof has been dissolved or suspended, and the like, and provides a convenient method for efficiently producing an optically active sulfoxide derivative having an extremely high enantiomer excess in high yield at an industrial large scale.

1 Claim, 24 Drawing Sheets

PROCESS FOR PRODUCING CRYSTAL

CROSS-REFERENCE TO RELATED APPLICATIONS

This application is a Division of application Ser. No. 12/492,735 filed Jun. 26, 2009, which is a Division of application Ser. No. 11/515,639, filed Sep. 5, 2006, now issued U.S. Pat. No. 7,569,696, which is a Division of application Ser. No. 10/275,334, filed Nov. 7, 2002, now issued U.S. Pat. No. 7,169,799, which is a U.S. National Stage of International Application No. PCT/JP01/04014, filed May 15, 2001, which applications are incorporated herein by reference.

TECHNICAL FIELD

The present invention relates to a production method of an optically active sulfoxide compound having an antiulcer activity.

BACKGROUND ART

As a method for producing (R)-2-[[[3-methyl-4-2,2,2-trifluoroethoxy)-2-pyridyl]methyl]sulfinyl]benzimidazole having an antiulcer activity [hereinafter sometimes to be referred to as an (R)-form] or (S)-2-[[[3-methyl-4-(2,2,2-trifluoroethoxy)-2-pyridyl]methyl]sulfinyl]benzimidazole having an antiulcer activity [hereinafter sometimes to be referred to as an (S)-form], for example, Japanese Patent Application under PCT laid open under kohyo No. Hei 11-508590 (WO 97/02261) describes a method for optically purifying a product prepared to be enriched in one enantiomer, which comprises adding a product prepared to contain either (+)-enantiomer or (−)-enantiomer in a greater amount than the other, namely, product prepared to be enriched in one enantiomer, to a solvent, selectively precipitating a racemic compound from the solvent utilizing the crystallinity of racemates, filtering and removing the precipitated racemic compound and removing the solvent to give a single enantiomer having an increased optical purity.
When an (R)-form or (S)-form is to be produced by asymmetric synthesis, 2-[[[3-methyl-4-(2,2,2-trifluoroethoxy)-2-pyridyl]methyl]thio]benzimidazole (hereinafter sometimes to be referred to as a sulfide form) is subjected to asymmetric oxidization to give the objective (R)- or (S)-form. In this case, an excess reaction product, 2-[[[3-methyl-4-(2,2,2-trifluoroethoxy)-2-pyridyl]methyl]sulfonyl]benzimidazole(hereinafter sometimes to be referred to as a sulfone form), is produced. Accordingly, the (R)-form or (S)-form obtained by asymmetric synthesis generally includes an unreacted sulfide form as an analogous substance and a sulfone form as an excess reaction product.

Generally, a sulfone form present in sulfoxide having an antiulcer activity is difficult to remove. For example, JP-A-2000-16992 discloses that, once sulfone is produced, the yield of the objective sulfoxide decreases, and separation and purification is problematically difficult because the physicochemical properties of the both are extremely similar to each other. Similarly in the case of an (R)-form or (S)-form, a column chromatography treatment and the like are essential for removing a sulfone form present as an analogous substance.

For example, in Example 21 of Japanese Patent Application under PCT laid-open under kohyo No. Hei 10-504290 (WO 96/02535), flush chromatography was applied to obtain the object substance from a solution containing a large amount of (−)-2-[[[3-methyl-4-(2,2,2-trifluoroethoxy)-2-pyridyl]methyl]sulfinyl]benzimidazole (11% of sulfide form and 7% of sulfone form present as analogous substances), after which various steps are applied to obtain the 99.5% ee objective substance in a yield of 29%. In Example 22 of this publication, flush chromatography was applied to obtain the objective substance from a solution containing a large amount of (+)-2-[[[3-methyl-4-(2,2,2-trifluoroethoxy)-2-pyridyl]methyl]sulfinyl]benzimidazole (13% of sulfide form and 8% of sulfone form present as analogous substances), after which various steps are applied to obtain the 99.6% ee objective substance in a yield of 14%.

As evidenced, conventional methods require industrially disadvantageous operations such as chromatography and the like are necessary for removing a sulfone form and the like, and the yield of the objective substance remains at a low level.

The conventional production methods are associated with problems that they indispensably require purification by column chromatography and the like to remove a sulfone form that resists separation and purification, and the objective optically active sulfoxide form shows a low enantiomer excess (optical purity) and low yield. Therefore, a production method of an (R)-form or (S)-form having an antiulcer activity, has been demanded which is industrially advantageous from the aspects of the amount of analogous substance present therein, enantiomer excess, yield, productivity, economic efficiency and the like.

DISCLOSURE OF THE INVENTION

The present inventors have studied the production methods of an (R)-form and an (S)-form from various aspects and have first found that an (R)-form and an (S)-form include a crystal (including solvate and hydrate) having a particular crystal form and showing physical properties different from those of a sulfone form; when the crystal having a particular crystal form is crystallized, a sulfone form that generally resists removal can be unexpectedly removed easily and the objective substance having an extremely high optical purity can be obtained; and further that this method is a production method fully satisfactory on an industrial scale and the like, which resulted in the completion of the present invention.

Accordingly, the present invention relates to

[1] a production method for a crystal of (R)-2-[[[3-methyl-4-(2,2,2-trifluoroethoxy)-2-pyridyl]methyl]sulfinyl]benzimidazole.n'H$_2$O (wherein n' is about 0 to about 0.1) or a salt thereof, which comprises obtaining the crystal by crystallization from an organic solvent solution or suspension in which (R)-2-[[[3-methyl-4-(2,2,2-trifluoroethoxy)-2-pyridyl]methyl]sulfinyl]benzimidazole.nH$_2$O (wherein n is about 0.1 to about 1.0) or a salt thereof has been dissolved or suspended;

[2] the production method according to the aforementioned [1], wherein (R)-2-[[[3-methyl-4-(2,2,2-trifluoroethoxy)-2-pyridyl]methyl]sulfinyl]benzimidazole.nH$_2$O (wherein n is about 0.1 to about 1.0) or a salt thereof is subjected to a dehydration step, followed by crystallization for the objective crystal;

[3] the production method according to the aforementioned [1], wherein the organic solvent comprises an acetic acid C$_{1-4}$ alkyl ester;

[4] the production method according to the aforementioned [3], wherein the acetic acid C$_{1-4}$ alkyl ester is ethyl acetate;

[5] the production method according to the aforementioned [1], wherein n is about 0.2 to about 0.8;

[6] the production method according to the aforementioned [1], wherein n is about 0.5;

[7] a production method for a crystal of (R)-2-[[[3-methyl-4-(2,2,2-trifluoroethoxy)-2-pyridyl]methyl]sulfinyl]benzimidazole.n'H$_2$O (wherein n' is about 0 to about 0.1) or a salt thereof, which is substantially free of (S)-2-[[[3-methyl-4-(2,2,2-trifluoroethoxy)-2-pyridyl]methyl]sulfinyl]benzimidazole or a salt thereof, which method comprises obtaining a crystal of (R)-2-[[[3-methyl-4-(2,2,2-trifluoroethoxy)-2-pyridyl]methyl]sulfinyl]benzimidazole.nH$_2$O (wherein n is about 0.1 to about 1.0) or a salt thereof by way of a selective crystallization from a solution or suspension comprising (R)-2-[[[3-methyl-4-(2,2,2-trifluoroethoxy)-2-pyridyl]methyl]sulfinyl]benzimidazole or a salt thereof in a greater amount than (S)-2-[[[3-methyl-4-(2,2,2-trifluoroethoxy)-2-pyridyl]methyl]sulfinyl]benzimidazole or a salt thereof, followed by crystallization for the objective crystal from an organic solvent solution or suspension in which the said obtained crystal has been dissolved or suspended;

[8] the production method according to the aforementioned [7], wherein the selective crystallization is conducted in an organic solvent containing water;

[9] the production method according to the aforementioned [8], wherein the organic solvent is one kind or more kinds selected from esters, ketones, ethers, hydrocarbons and aromatic hydrocarbons;

[10] the production method according to the aforementioned 1 or 7, wherein the crystal of (R)-2-[[[3-methyl-4-(2,2,2-trifluoroethoxy)-2-pyridyl]methyl]sulfinyl]benzimidazole.n'H$_2$O (wherein n' is about 0 to about 0.1) shows characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction;

[11] a production method for a crystal of (R)-2-[[[3-methyl-4-(2,2,2-trifluoroethoxy)-2-pyridyl]methyl]sulfinyl]benzimidazole or a salt thereof, which is substantially free of (S)-2-[[[3-methyl-4-(2,2,2-trifluoroethoxy)-2-pyridyl]methyl]sulfinyl]benzimidazole or a salt thereof, which method comprises obtaining a crystal of (R)-2-[[[3-methyl-4-(2,2,2-trifluoroethoxy)-2-pyridyl]methyl]sulfinyl]benzimidazole or a salt thereof by a selective crystallization from a solution comprising (R)-2-[[[3-methyl-4-(2,2,2-trifluoroethoxy)-2-pyridyl]methyl]sulfinyl]benzimidazole or a salt thereof in a greater amount than (S)-2-[[[3-methyl-4-(2,2,2-trifluoroethoxy)-2-pyridyl]methyl]sulfinyl]benzimidazole or a salt thereof and subjecting the obtained crystal to a dehydration step, followed by crystallization for the objective crystal;

[12] a production method for a crystal of (S)-2-[[[3-methyl-4-(2,2,2-trifluoroethoxy)-2-pyridyl]methyl]sulfinyl]benzimidazole.m'H$_2$O (wherein m' is about 0 to about 0.1) or a salt thereof, which comprises obtaining the objective crystal by crystallization from an organic solvent solution or suspension in which (S)-2-[[[3-methyl-4-(2,2,2-trifluoroethoxy)-2-pyridyl]methyl]sulfinyl]benzimidazole.mH$_2$O (wherein m is about 0 to about 0.1) or a salt thereof has been dissolved or suspended;

[13] the production method according to the aforementioned 12, wherein (S)-2-[[[3-methyl-4-(2,2,2-trifluoroethoxy)-2-pyridyl]methyl]sulfinyl]benzimidazole.mH$_2$O (wherein m is about 0.1 to about 1.0) or a salt thereof is subjected to a dehydration step, followed by crystallization for the objective crystal;

[14] the production method according to the aforementioned 12, wherein the organic solvent comprises an acetic acid $C_{1-4}$ alkyl ester;

[15] the production method according to the aforementioned 14, wherein the acetic acid $C_{1-4}$ alkyl ester is ethyl acetate;

[16] the production method according to the aforementioned 12, wherein m is about 0.2 to about 0.8;

[17] the production method according to the aforementioned 12, wherein m is about 0.5;

[18] a production method for a crystal of (S)-2-[[[3-methyl-4-(2,2,2-trifluoroethoxy)-2-pyridyl]methyl]sulfinyl]benzimidazole.m'H$_2$O (wherein m' is about 0 to about 0.1) or a salt thereof, which is substantially free of (R)-2-[[[3-methyl-4-(2,2,2-trifluoroethoxy)-2-pyridyl]methyl]sulfinyl]benzimidazole or a salt thereof, which method comprises obtaining a crystal of (S)-2-[[[3-methyl-4-(2,2,2-trifluoroethoxy)-2-pyridyl]methyl]sulfinyl]benzimidazole.mH$_2$O (wherein m is about 0.1 to about 1.0) or a salt thereof by a selective crystallization from a solution or suspension comprising (S)-2-[[[3-methyl-4-(2,2,2-trifluoroethoxy)-2-pyridyl]methyl]sulfinyl]benzimidazole or a salt thereof in a greater amount than (R)-2-[[[3-methyl-4-(2,2,2-trifluoroethoxy)-2-pyridyl]methyl]sulfinyl]benzimidazole or a salt thereof, followed by crystallization for the objective crystal from an organic solvent solution or suspension in which the obtained crystal has been dissolved or suspended;

[19] the production method according to the aforementioned 18, wherein the selective crystallization is conducted in an organic solvent containing water;

[20] the production method according to the aforementioned 19, wherein the organic solvent is one kind or more kinds selected from esters, ketones, ethers, hydrocarbons and aromatic hydrocarbons;

[21] the production method according to the aforementioned 12 or 18, wherein the crystal of (S)-2-[[[3-methyl-4-(2,2,2-trifluoroethoxy)-2-pyridyl]methyl]sulfinyl]benzimidazole.m'H$_2$O (wherein m' is about 0 to about 0.1) shows characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction;

[22] a production method for a crystal of (S)-2-[[[3-methyl-4-(2,2,2-trifluoroethoxy)-2-pyridyl]methyl]sulfinyl]benzimidazole or a salt thereof, which is substantially free of (R)-2-[[[3-methyl-4-(2,2,2-trifluoroethoxy)-2-pyridyl]methyl]sulfinyl]benzimidazole or a salt thereof, which method comprises obtaining a crystal of (S)-2-[[[3-methyl-4-(2,2,2-trifluoroethoxy)-2-pyridyl]methyl]sulfinyl]benzimidazole or a salt thereof by a selective crystallization from a solution comprising (S)-2-[[[3-methyl-4-(2,2,2-trifluoroethoxy)-2-pyridyl]methyl]sulfinyl]benzimidazole or a salt thereof in a greater amount than (R)-2-[[[3-methyl-4-(2,2,2-trifluoroethoxy)-2-pyridyl]methyl]sulfinyl]benzimidazole or a salt thereof, and subjecting the obtained crystal to a dehydration step, followed by crystallization for the objective crystal;

[23] the production method according to the aforementioned 7, 11, 18 or 22, wherein (R)-2-[[[3-methyl-4-(2,2,2-trifluoroethoxy)-2-pyridyl]methyl]sulfinyl]benzimidazole or a salt thereof or (S)-2-[[[3-methyl-4-(2,2,2-trifluoroethoxy)-2-pyridyl]methyl]sulfinyl]benzimidazole or a salt thereof in the solution or suspension shows an enantiomer excess of not less than about 80% ee;

[24] the production method according to the aforementioned 7, 11, 18 or 22, wherein the crystal obtained by the selective crystallization is (1) a crystal showing characteristic peaks at interplanar spacings (d) of 5.88, 4.70, 4.35, 3.66 and 3.48 Angstroms in powder X-ray diffraction;

(2) a crystal showing characteristic peaks at interplanar spacings (d) of 8.33, 6.63, 5.86 and 4.82 Angstroms in powder X-ray diffraction; or
(3) a mixture of the crystals of the above (1) and (2);
[25] the production method according to the aforementioned 7, 11, 18 or 22, wherein the crystal obtained by the selective crystallization is further subjected to one or more times of a crystallization step;
[26] a crystal of (R)-2-[[[3-methyl-4-(2,2,2-trifluoroethoxy)-2-pyridyl]methyl]sulfinyl]benzimidazole.nH$_2$O (wherein n is about 0.1 to about 1.0) or a salt thereof;
[27] a crystal of (S)-2-[[[3-methyl-4-(2,2,2-trifluoroethoxy)-2-pyridyl]methyl]sulfinyl]benzimidazole.mH$_2$O (wherein m is about 0.1 to about 1.0) or a salt thereof;
[28] the crystal according to the aforementioned 26 or 27, which shows characteristic peaks at interplanar spacings (d) of 5.88, 4.70, 4.35, 3.66 and 3.48 Angstroms in powder X-ray diffraction;
[29] the crystal according to the aforementioned 26 or 27, which is a crystal shows characteristic peaks at interplanar spacings (d) of 8.33, 6.63, 5.86 and 4.82 Angstroms in powder X-ray diffraction.

Figure 1:
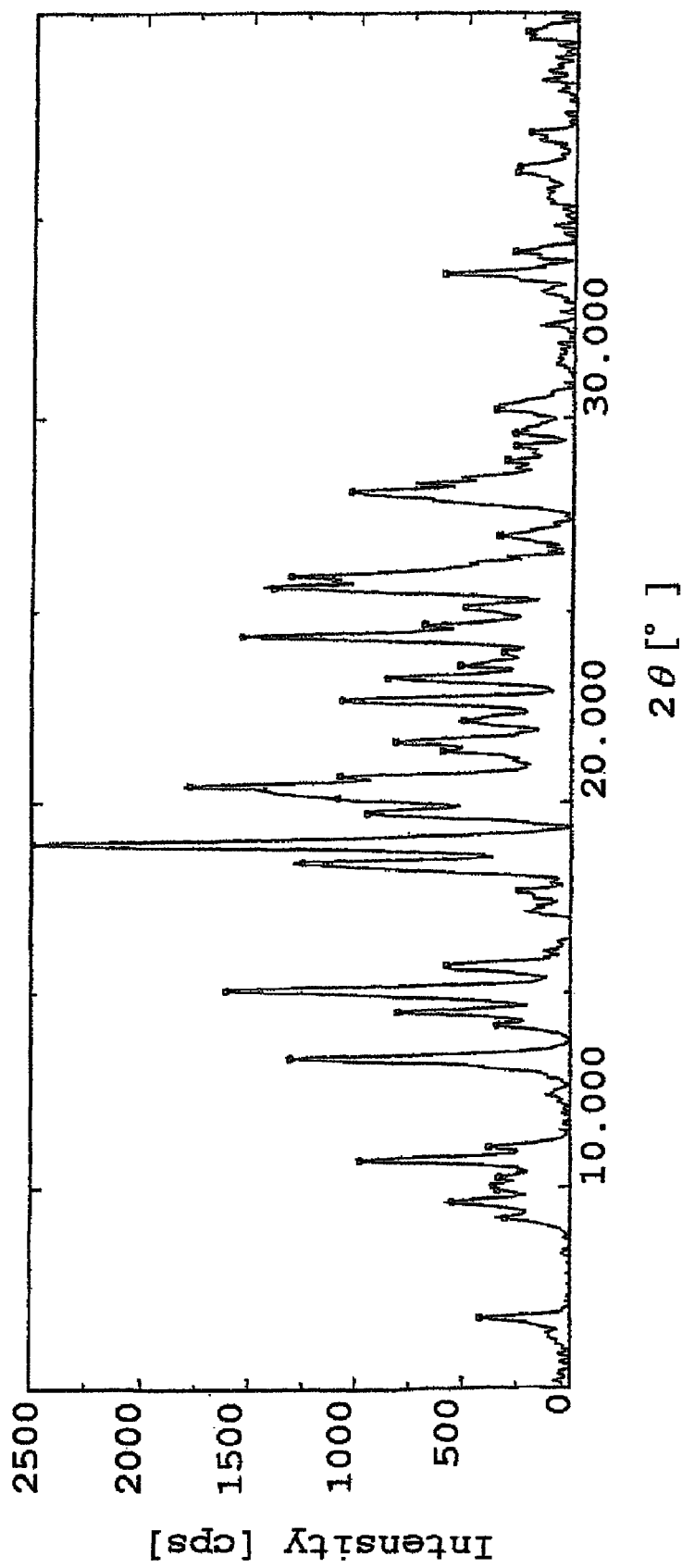
FIG. 1 shows a powder X-ray diffraction chart of the wet crystal of Example 3(2).

As the "salt" of (R)-form and the "salt" of (S)-form, pharmaceutically acceptable salts are preferable. For example, a salt with an inorganic base, a salt with an organic base, a salt with a basic amino acid and the like are mentioned.

Preferable examples of the salt with an inorganic base include alkali metal salts (e.g., sodium salt, potassium salt etc.); alkaline earth metal salts (e.g., calcium salt, magnesium salt etc.); ammonium salt; and the like.

Preferable examples of the salt with an organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with an organic base include salts with arginine, lysin, ornithine and the like.

Of these, preferred are alkali metal salt and alkaline earth metal salt. Particularly, a sodium salt is preferable.

An (R)-form.nH$_2$O (wherein n is about 0.1 to about 1.0) or a salt thereof can be produced by selective crystallization for a crystal of an (R)-form.nH$_2$O (wherein n is about 0.1 to about 1.0) or a salt thereof from "a solution or suspension containing the (R)-form or a salt thereof in a greater amount than an (S)-form or a salt thereof".

In addition, an (S)-form.mH$_2$O (wherein m is about 0.1 to about 1.0) or a salt thereof can be produced by selective crystallization for a crystal of the (S)-form.mH$_2$O (wherein m is about 0.1 to about 1.0) or a salt thereof from "a solution or suspension containing the (S)-form or a salt thereof in a greater amount than an (R)-form or a salt thereof".

As used herein, ".nH$_2$O" and ".mH$_2$O" mean n-hydrate and m-hydrate, respectively.

The "solution or suspension containing the (R)-form or a salt thereof in a greater amount than an (S)-form or a salt thereof" and the "solution or suspension containing the (S)-form or a salt thereof in a greater amount than an (R)-form or a salt thereof" can be produced by a method known per se, such as the method described in Japanese Patent Application under PCT laid-open under kohyo No. Hei 10-504290 (WO 96/02535) and the like or a method analogous thereto, or by the following method.

2-[[[3-Methyl-4-(2,2,2-trifluoroethoxy)-2-pyridinyl]-methyl]thio]-1H-benzimidazole and an excess amount (about 1.5-10 equimolar amount) of an oxidizing agent (e.g., peroxides such as hydrogen peroxide, tert-butylhydroperoxide, cumene hydroperoxide etc., and the like) are reacted in the presence of a catalyst for asymmetric induction (e.g., a complex of optically active diol, titanium(IV) alkoxide and water and the like), an organic solvent [e.g., alcohols such as methanol, ethanol, propanol, isopropanol etc.; aromatic hydrocarbons such as benzene, toluene, xylene etc.; ethers such as diethyl ether, diisopropyl ether, butylmethyl ether, dioxane, tetrahydrofuran etc.; esters such as ethyl acetate, methyl acetate etc.; ketones such as acetone, methyl isobutyl ketone etc.; halogenated hydrocarbons such as chloroform, dichloromethane, ethylene dichloride, carbon tetrachloride etc.; amides such as N,N-dimethylformamide etc.; sulfoxides such as dimethyl sulfoxide etc.; acetic acid etc.] and a base [e.g., inorganic bases such as alkali metal carbonate (e.g., potassium carbonate, sodium carbonate etc.), alkali metal hydroxides (e.g., sodium hydroxide, potassium hydroxide etc.), alkali metal hydride (e.g., sodium hydride, potassium hydride etc.), and the like; organic bases such as alkali metal alkoxides (e.g., sodium methoxide, sodium ethoxide etc.), alkali metal carboxylate (e.g., sodium acetate etc.), amines (e.g., piperidine, piperazine, pyrrolidine, morpholine, triethylamine, tripropylamine, tributylamine, trioctylamine, diisopropylethylamine, dimethylphenylamine etc.), pyridines (e.g., pyridine, dimethylaminopyridine etc.), and the like; basic amino acids (e.g., arginine, lysin, ornithine etc.); and the like] at about −20 to 20° C. for about 0.1 to 50 hr to give the "solution or suspension containing the (R)-form or a salt thereof in a greater amount than the (S)-form or a salt thereof" and the "solution or suspension containing an (S)-form or a salt thereof in a greater amount than an (R)-form or a salt thereof".

The "(R)-form or a salt thereof" and "(S)-form or a salt thereof" in the above-mentioned solution or suspension may be either a solid (crystal, amorphous) or an oily substance, and may or may not be isolated or purified.

As a solvent to prepare the "solution or suspension", for example, water, esters, ketones, phenols, alcohols, ethers, aromatic hydrocarbons, amides, sulfoxides, hydrocarbons, nitriles, halogenated hydrocarbons, pyridines, a mixture of two or more thereof and the like are used.

The enantiomer excess of the (R)-form or a salt thereof or (S)-form or a salt thereof in a solution or suspension is, for example, not less than about 80% ee, preferably not less than about 90% ee.

The method for "selective crystallization" includes, for example, a method of stirring the solution or suspension, a method of adding a seed crystal to the solution or suspension, a method of changing the temperature of the solution or suspension, a method of changing the solvent composition of the solution or suspension, a method of reducing the liquid amount of the solution or suspension, or a combination of two or more of these methods and the like.

As the "method of stirring the solution or suspension", for example, a method comprising stirring a solution or a suspension containing one of (R)-form or a salt thereof and an (S)-form or a salt thereof in a greater amount than the other at about −80 to 120° C., preferably about −20 to 60° C., for about 0.01 to 100 hr, preferably about 0.1 to 10 hr, is mentioned.

As the "method of adding a seed crystal to the solution or suspension", for example, a method comprising adding, (1) a crystal showing characteristic peaks at interplanar spacings (d) of 5.88, 4.70, 4.35, 3.66 and 3.48 Angstroms in powder X-ray diffraction, (2) a crystal showing characteristic peaks at interplanar spacings (d) of 8.33, 6.63, 5.86 and 4.82 Angstroms in powder X-ray diffraction, (3) a mixture of the crystals of the aforementioned (1) and (2), or (4) a solid that converts to the aforementioned (1) to (3) in a solution or suspension (e.g., a crystal showing characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction, a crystal showing characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction, a crystal showing characteristic peaks at interplanar spacings (d) of 8.37, 4.07, 5.65, 5.59, 5.21, 4.81 and 4.21 Angstroms in powder X-ray diffraction and the like), as a seed crystal, to a solution or a suspension containing one of (R)-form or a salt thereof and an (S)-form or a salt thereof in a greater amount than the other, is mentioned.

As the "method of changing the temperature of the solution or suspension", for example, a method for changing the temperature of a solution or a suspension containing one of an (R)-form or a salt thereof and an (S)-form or a salt thereof in a greater amount than the other, preferably a method for cooling (e.g., lower the liquid temperature by 5 to 100° C.), are mentioned.

As the "method of changing the solvent composition of the solution or suspension", for example, a method for adding water, an organic solvent (e.g., esters, ketones, phenols, alcohols, ethers, aromatic hydrocarbons, amides, sulfoxides, hydrocarbons, nitriles, halogenated hydrocarbons, pyridines or a mixture of two or more kinds of these; preferably a low polarity organic solvent (e.g., esters, ethers, aromatic hydrocarbons, hydrocarbons, halogenated hydrocarbons or a mixture of two or more kinds thereof, and the like), ketones or a mixture of two or more kinds thereof) to a solution or a suspension containing one of an (R)-form or a salt thereof and an (S)-form or a salt thereof in a greater amount than the other, is mentioned. Preferably, a method for adding one or more kinds selected from the organic solvents such as esters, ketones, ethers and hydrocarbons in the presence of water, is mentioned.

As a method for addition, a method comprising dropwise adding, under stirring, water, an organic solvent or a mixture thereof to a solution or a suspension containing one of an (R)-form or a salt thereof and an (S)-form or a salt thereof in a greater amount than the other, a method comprising dropwise adding, under stirring, water, an organic solvent or a mixture thereof to a solution or a suspension containing one of an (R)-form or a salt thereof and an (S)-form or a salt thereof in a greater amount than the other and the like are mentioned.

As the "method of reducing the liquid amount of the solution or suspension", for example, a method comprising removing and evaporating the solvent from a solution or a suspension containing one of an (R)-form or a salt thereof and an (S)-form or a salt thereof in a greater amount than the other, and the like are mentioned.

Of these, preferred are (i) a method for stirring a solution or suspension,
(ii) a method for changing the solvent composition of a solution or suspension,
(iii) a method comprising both a method for stirring a solution or suspension and a method for adding a seed crystal to a solution or suspension,
(iv) a method comprising both a method for stirring a solution or suspension and a method for changing the temperature of a solution or suspension,
(v) a method comprising both a method for stirring a solution or suspension and a method for changing the solvent composition of a solution or suspension,
(vi) a method comprising both a method for stirring a solution or suspension and a method for reducing the liquid amount of a solution or suspension,
(vii) a method comprising a method for stirring a solution or suspension, a method for changing the temperature of a solution or suspension and a method for adding a seed crystal to a solution or suspension,
(viii) a method comprising a method for stirring a solution or suspension, a method for changing the solvent composition of a solution or suspension and a method for adding a seed crystal to a solution or suspension,
(ix) a method comprising a method for stirring a solution or suspension, a method for reducing the liquid amount of a solution or suspension and a method for adding a seed crystal to a solution or suspension,
(x) a method comprising a method for stirring a solution or suspension, a method for changing the temperature of a solution or suspension and a method for changing the solvent composition of a solution or suspension, (xi) a method comprising a method for stirring a solution or suspension, a method for changing the temperature of a solution or suspension, a method for changing the solvent composition of a solution or suspension and a method for adding a seed crystal to a solution or suspension, (xii) a method comprising a method for stirring a solution or suspension, a method for changing the temperature of a solution or suspension and a method for reducing the liquid amount of a solution or suspension, and (xiii) a method comprising a method for stirring a solution or suspension, a method for changing the temperature of a solution or suspension, a method for reducing the liquid amount of a solution or suspension and a method for adding a seed crystal to a solution or suspension.

Of the above-mentioned methods, the methods of (ii), (v) and (x) are preferable, and the method of (x) is more preferable.

More preferable embodiment of the method of "selective crystallization" is shown in the following.

In a solution or a suspension containing one of an (R)-form or a salt thereof and an (S)-form or a salt thereof in a greater amount than the other, the organic solvent contained in the solution or suspension is particularly preferably a mixture of 1 or 2 or 3 kinds selected from esters, ketones, ethers, hydrocarbons and aromatic hydrocarbons, more preferably $C_{6-10}$ alkane (e.g., hexane, heptane, octane etc.), t-butyl methyl ether, diethyl ether, diisopropyl ether, acetone, toluene, xylene, a mixture thereof and the like.

The organic solvent to be added in the presence of water is particularly preferably a mixture of hydrocarbons (e.g., $C_{6-10}$ alkane such as hexane, heptane, octane etc., and the like) and ethers (e.g., t-butyl methyl ether, diethyl ether, diisopropyl ether etc.), ketones (e.g., acetone etc.) and the like.

As a method for addition, a mixture of water and an organic solvent is added dropwise under stirring to a solution or suspension containing one of an (R)-form or a salt thereof and an (S)-form or a salt thereof in a greater amount than the other, or a solution or suspension containing one of an (R)-form or a salt thereof and an (S)-form or a salt thereof in a greater amount than the other is added dropwise under stirring to a mixture of water and an organic solvent, and the like. When desired, water may be further added dropwise.

Therefore, selective crystallization is preferably conducted in an organic solvent containing water.

By the method of selective crystallization, when, for example, an (R)-form or a salt thereof or (S)-form or a salt thereof obtained by asymmetric synthesis is used, the amount of an analogous substance (e.g., 2-[[[3-methyl-4-(2,2,2-trifluoroethoxy)-2-pyridyl]methyl]thio]benzimidazole and (or) 2-[[[3-methyl-4-(2,2,2-trifluoroethoxy)-2-pyridyl]methyl]sulfonyl]benzimidazole and the like) in the precipitated crystals can be reduced.

The crystal obtained by crystallization can be separated and collected by the method of, for example, filtration, centrifugation and the like.

Examples of the crystal obtained by selective crystallization according to the above-mentioned method include an (R)-form.nH$_2$O (wherein n is about 0.1 to about 1.0), a salt thereof, an (S)-form.mH$_2$O (wherein m is about 0.1 to about 1.0), a salt thereof and the like.

The "n" or "m" is preferably about 0.2 to about 0.8, particularly preferable about 0.5.

By crystallization from an organic solvent solution or suspension wherein the thus-obtained crystal [e.g., crystal of the above-mentioned (R)-form.nH$_2$O (wherein n is about 0.1 to about 1.0) or a salt thereof or an (S)-form.mH$_2$O (wherein m is about 0.1 to about 1.0) or a salt thereof] has been dissolved or suspended, a crystal of an (R)-form.n'H$_2$O (wherein n' is about 0 to about 0.1) or a salt thereof or an (S)-form.m'H$_2$O (wherein m' is about 0 to about 0.1) or a salt thereof can be produced.

Here, the relationship between n and n', and m and m' in the above-mentioned steps is n>n' and m>m'. Therefore, for example, when n or m is 0.1, the corresponding n' and m' is less than 0.1.

The organic solvent to be used for dissolving or suspending includes, for example, esters, ketones, phenols, alcohols, ethers, aromatic hydrocarbons, amides, sulfoxides, hydrocarbons, nitriles, halogenated hydrocarbons, pyridines, a mixture of two or more thereof, and the like, preferably esters, hydrocarbons and a mixture thereof. Of these, an organic solvent containing esters such as acetic acid $C_{1-4}$ alkyl ester (e.g., ethyl acetate, propyl acetate, butyl acetate etc.) and the like are preferable.

More preferred are acetic acid $C_{1-4}$ alkyl ester (e.g., ethyl acetate, propyl acetate, butyl acetate etc.), $C_{6-8}$ hydrocarbons (e.g., $C_{6-8}$ alkane such as hexane, heptane, octane etc., and the like) and a mixture thereof and the like.

For crystallization, for example, a crystal of the above-mentioned (R)-form.nH$_2$O (wherein n is about 0.1 to about 1.0) or a salt thereof or an (S)-form.mH$_2$O (wherein m is about 0.1 to about 1.0) or a salt thereof is preferably dissolved or suspended in an organic solvent, subjected to a dehydration step and then subjected to crystallization. In the production method of the present invention, the step for "crystallization from an organic solvent solution or suspension" may include the "dehydration step" and the "crystallization step".

The dehydration step may include a general dehydration method, such as a method comprising dissolving or suspending the above-mentioned crystal of (R)-form.nH$_2$O (wherein n is about 0.1 to about 1.0) or a salt thereof or (S)-form.mH$_2$O (wherein m is about 0.1 to about 1.0) or a salt thereof in an organic solvent such as esters, ketones, phenols, alcohols, ethers, aromatic hydrocarbons, amides, sulfoxides, hydrocarbons, nitriles, halogenated hydrocarbons, pyridines, a mixture of two or more kinds thereof and the like, preferably esters such as acetic acid $C_{1-4}$ alkyl ester (e.g., ethyl acetate, propyl acetate, butyl acetate etc.) and the like, which is followed by a method of partitioning, a method of concentration, a method using a dehydrating agent [e.g., anhydrous magnesium sulfate, anhydrous sodium sulfate, molecular sieve (product name)], or a combination of these methods and the like.

The above-mentioned method of concentration is preferably carried out under reduced pressure.

After the dehydration step, the objective crystal can be obtained by crystallization (recrystallization) from a solution or suspension of the obtained crystal in an organic solvent [e.g., esters, ketones, phenols, alcohols, ethers, aromatic hydrocarbons, amides, sulfoxides, hydrocarbons, nitriles, halogenated hydrocarbons, pyridines, a mixture of two or more kinds thereof and the like, preferably hydrocarbons such as $C_{6-8}$ hydrocarbons (e.g., $C_{6-8}$ alkane such as hexane, heptane, octane etc., and the like) and the like].

In the following, a step for crystallization from an organic solvent solution or suspension, wherein a crystal of an (R)-form.nH$_2$O (wherein n is about 0.1 to about 1.0) or a salt thereof or an (S)-form.mH$_2$O (wherein m is about 0.1 to about 1.0) or a salt thereof has been dissolved or suspended, is described in detail.

First, a crystal of an (R)-form.nH$_2$O (wherein n is about 0.1 to about 1.0) or a salt thereof or an (S)-form.mH$_2$O (wherein m is about 0.1 to about 1.0) or a salt thereof obtained by the above-mentioned method, as it is or after drying as necessary, is subjected to a crystallization step (once or more, preferably two or three times) (the crystallization step may include a step of dissolving or suspending in a solvent, a recrystallization step, a dehydration step and the like) as necessary. In one or more times of the crystallization step, a dehydration step is preferably included immediately before the final crystallization (recrystallization) step.

For the "drying", for example, vacuum drying, through-flow drying, drying by heating, air drying and the like are mentioned.

Specifically, the obtained crystal or a dried crystal thereof is dissolved or suspended in a solvent (e.g., water, esters, ketones, phenols, alcohols, ethers, aromatic hydrocarbons, amides, sulfoxides, hydrocarbons, nitriles, halogenated hydrocarbons, pyridines or a mixture of two or more kinds thereof and the like, preferably a mixture of water and one or more (preferably two or three) kinds of organic solvent(s) selected from hydrocarbons [e.g., $C_{6-8}$ hydrocarbons (e.g., $C_{6-8}$ alkane such as hexane, heptane, octane etc., and the like) and the like], aromatic hydrocarbons (e.g., toluene, xylene etc.), ketones (e.g., acetone etc.) and ethers (e.g., t-butyl methyl ether, diethyl ether, diisopropyl ether), and after subjecting to a dehydration step as necessary, a crystal is obtained by crystallization.

Preferably, the obtained crystal or a dried crystal thereof is subjected to the above-mentioned crystallization step (once or more, preferably two or three times), subjected to a dehydration step immediately before the final crystallization step (recrystallization), and the objective crystal is obtained by crystallization.

For the "dehydration", methods similar to the above-mentioned dehydration methods are exemplified.

For the "crystallization" method in the above-mentioned once or more, preferably two or three times of crystallization, the method described in the aforementioned "method for selective crystallization" is mentioned. The method for crystallization to obtain the objective crystal after subjecting to the dehydration step preferably comprises recrystallization from a solution or suspension of the crystal obtained by dehydration step in an organic solvent [e.g., esters, ketones, phenols, alcohols, ethers, aromatic hydrocarbons, amides, sulfoxides, hydrocarbons, nitriles, halogenated hydrocarbons, pyridines, a mixture of two or more kinds thereof and the like, preferably hydrocarbons such as $C_{6-8}$ hydrocarbons (e.g., $C_{6-8}$ alkane such as hexane, heptane, octane etc., and the like), and the like].

As the crystal obtained by the above-mentioned crystallization step (recrystallization), there may be included (1) a crystal showing characteristic peaks at interplanar spacings (d) of 5.88, 4.70, 4.35, 3.66 and 3.48 Angstroms in powder X-ray diffraction of undried crystal,
(2) a crystal showing characteristic peaks at interplanar spacings (d) of 8.33, 6.63, 5.86 and 4.82 Angstroms in powder X-ray diffraction of undried crystal,
(3) a mixture of the crystals of the aforementioned (1) and (2) or
(4) a crystal showing characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction and the like.

The amount of analogous substances in the crystal is less than 1 wt %, preferably less than 0.4 wt %.

The crystal obtained by the above-mentioned crystallization step (e.g., recrystallization etc.) can be separated and collected by a method such as filtration, centrifugation and the like.

The crystal (objective crystal) obtained by the above-mentioned final crystallization step (recrystallization) may be a crystal of an (R)- or an (S)-form showing characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction and the like.

The separated and collected crystal can be dried by a method such as vacuum drying, through-flow drying, drying by heating, air drying and the like.

The "crystal of an (R)-form.n'$H_2O$ (wherein n' is about 0 to about 0.1) or a salt thereof" or "a crystal of an (R)-form or a salt thereof, which is substantially free of an (S)-form or a salt thereof", which is finally crystallized out in the present invention, means a crystal of an (R)-form or a salt thereof which contains an (S)-form or a salt thereof in a proportion of 0 to 3%, preferably 0 to 1%.

The "crystal of an (S)-form.m'$H_2O$ (wherein m' is about 0 to about 0.1) or a salt thereof" or "a crystal of an (S)-form or a salt thereof, which is substantially free of an (R)-form or a salt thereof", which is crystallized out in the present invention means a crystal of an (S)-form or a salt thereof which contains an (R)-form or a salt thereof in a proportion of 0-1%.

As used herein, the above-mentioned ".n'$H_2O$" and ".m'$H_2O$" mean n'-hydrate and m'-hydrate, respectively.

In the production method of the present invention, a crystal almost free of hydrate water or an anhydrous crystal, such as an (R)-form.n'$H_2O$ (wherein n' is about 0 to about 0.1) or a salt thereof or an (S)-form.m'$H_2O$ (wherein m' is about 0 to about 0.1) or a salt thereof, can be obtained by, for example, the above-mentioned one or more times, preferably two or three times, of the crystallization step, then a dehydration step and the final crystallization step. Such crystal is exemplified by a crystal showing characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction.

The "n'" and "m'" are preferably about 0 to about 0.1. Particularly, n is 0 and m is 0, or an anhydrous crystal, is more preferable.

As the aforementioned "esters", for example, acetic acid $C_{1-4}$ alkyl ester such as methyl acetate, ethyl acetate, propyl acetate, isopropyl acetate, butyl acetate, isobutyl acetate and the like, ethyl formate and the like can be mentioned.

As the aforementioned "ketones", for example, acetone, methyl ethyl ketone, methyl isopropyl ketone, methyl butyl ketone, methyl isobutyl ketone and the like can be mentioned.

As the aforementioned "phenols", for example, anisole and the like can be mentioned.

As the aforementioned "alcohols", for example, lower alcohols such as methanol, ethanol, 1-propanol, 2-propanol, 1-butanol, 2-butanol, 2-methyl-1-propanol, pentanol, 3-methyl-1-butanol and the like; lower alcohols substituted by $C_{1-3}$ alkoxy such as 2-methoxyethanol, 2-ethoxyethanol and the like; ethylene glycol and the like can be mentioned.

As the aforementioned "ethers", for example, t-butyl methyl ether, diethyl ether, 1,1-diethoxypropane, 1,1-dimethoxypropane, 2,2-dimethoxypropane, isopropyl ether, tetrahydrofuran, methyltetrahydrofuran and the like can be mentioned.

As the aforementioned "aromatic hydrocarbons", for example, chlorobenzene, toluene, xylene, cumene and the like can be mentioned.

As the aforementioned "amides", for example, formamide, N,N-dimethylacetamide, N,N-dimethylformamide, N-methylpyrrolidone and the like can be mentioned.

As the aforementioned "sulfoxides", for example, dimethyl sulfoxide and the like can be mentioned.

As the aforementioned "hydrocarbons", for example, $C_{3-10}$ alkane such as propane, butane, pentane, hexane, heptane, octane, isooctane and the like, preferably $C_{6-10}$ alkane, can be mentioned.

As the aforementioned "nitriles", for example, acetonitrile and the like can be mentioned.

As the aforementioned "halogenated hydrocarbons", for example, $C_{1-6}$ alkane optionally substituted by 1 to 5 halogens (e.g., fluorine, chlorine, bromine, iodine), such as chloroform, dichloromethane, dichloroethene, trichloroethene and the like, can be mentioned.

As the aforementioned "pyridines", for example, pyridine and the like can be mentioned.

The crystal obtained by crystallization by the method of the present invention or a dried crystal thereof is useful as a pharmaceutical product because it does not substantially contain an enantiomer, has a superior antiulcer activity, a gastric acid secretion-inhibitory action, a mucosa-protecting action, an anti-*Helicobacter pylori* action and the like and shows low toxicity. A dried crystal of an (R)-form or an (S)-form or a salt thereof is stabler than a crystal as just crystallized (undried crystal) of an (R)-form or an (S)-form or a salt thereof. Therefore, for use as a pharmaceutical product, a crystal as a dried product of an (R)-form or an (S)-form or a salt thereof is preferably used. For example, a crystal or a dried crystal obtained by crystallization by the method of the present invention is useful for the prophylaxis or treatment of digestive ulcer (e.g., gastric ulcer, duodenal ulcer, stomach ulcer, Zollinger-Ellison syndrome, etc.), gastritis, reflux esophagitis, NUD (Non-Ulcer Dyspepsia), gastric cancer (inclusive of gastric cancer caused by promotion of interleukin-1β production due to genetic polymorphism of interleukin-1) and gastric MALT lymphoma; eradication of *Helicobacter pylori*; suppression of upper gastrointestinal hemorrhage due to digestive ulcer, acute stress ulcer and hemorrhagic gastritis; suppression of upper gastrointestinal hemorrhage due to invasive stress (stress from major surgery necessitating intensive management after surgery, and from cerebral vascular disorder, head trauma, multiple organ failure and extensive burn necessitating intensive treatment); treatment and prevention of ulcer caused by a nonsteroidal anti-inflammatory agent; treatment and prevention of hyperacidity and ulcer due to postoperative stress; pre-anesthetic administration and the like, in mammals (e.g., human, simian, sheep, bovine, horse, dog, cat, rabbit, rat, mouse and the like). For eradication of *Helicobacter pylori*, the crystal or dry crystal obtained by the method of the present invention and antibiotic penicillins (e.g., amoxicillin etc.) and antibiotic erythromycins (e.g., clarithromycin, etc.) are preferably used.

EXAMPLES

The present invention is described in more detail in the following by means of Reference Examples and Examples, which are not to be construed as limitative.

The powder X-ray diffraction was measured using an X-ray Diffractometer RINT Ultima+ (Rigaku).

The enantiomer excess (fee) was measured by high performance liquid chromatography using the optically active column under the following condition (A).

The amount of the sulfide form and sulfone form present therein was measured by high performance liquid chromatography using the optically active column under the following condition (A) or high performance liquid chromatography under condition (B).

high performance liquid chromatography condition (A);

column: CHIRALCEL OD (manufactured by Daicel Chemical Industries, Ltd.)
mobile phase: hexane/ethanol=90/10
flow rate: 1.0 ml/min
detection: UV 285 nm
high performance liquid chromatography condition (B);
column: Capcell Pak (manufactured by Shiseido Company, Ltd.)
mobile phase: acetonitrile:water:triethylamine mixed solution (50:50:1) adjusted to pH 7.0 by addition of phosphoric acid.
flow rate: 1.0 ml/min
detection: UV 285 nm Reference Example 1

Production of Solution Containing (R)-Form or (S)-Form by Asymmetric Oxidization Under a nitrogen atmosphere, 2-[[[3-methyl-4-(2,2,2-trifluoroethoxy)-2-pyridyl]methyl]thio]benzimidazole (50.0 g, 0.14 mol, containing 16.7 mg of water), toluene (250 ml), water (283 mg, 0.016 mol, total amount of water 0.017 mol), diethyl (+)-tartrate (10.6 ml, 0.062 mol) were mixed, and the mixture was stirred at 50 to 55° C. for 30 min. Under a nitrogen atmosphere, titanium(IV) isopropoxide (8.29 ml, 0.028 mol) was added and the mixture was stirred at 50 to 55° C. for 1 hr. Under nitrogen atmosphere and under cooling, diisopropylethylamine (8.13 ml, 0.047 mol) was added to the obtained mixture and cumene hydroperoxide (76.50 ml, content 82%, 0.43 mol) was added at −10 to 0° C. The mixture was stirred at −10 to 10° C. for 4.5 hr to allow reaction.

As a result of the analysis of the reaction mixture by high performance liquid chromatography (condition (A)), 0.74% of a sulfide form and 1.46% of a sulfone form were present as analogous substances in the reaction mixture, and other analogous substances were not present. The enantiomer excess of an (R)-form in the reaction mixture was 96.5% ee.

Example 1

Production Method of (R)-Form

To the reaction mixture obtained according to Reference Example 1 [containing 14.63 g of a mixture of an (R)-form and an (S)-form, enantiomer excess 97.0% ee] was added dropwise heptane (200 ml) at 0 to 10° C., and the mixture was stirred at the same temperature for 2 hr. After stirring, the precipitated crystal was collected by filtration to give a wet crystal of an (R)-form (yield (amount) after drying: 12.96 g, yield (percentage) after drying: 88.6%) having the following interplanar spacing (d) in powder X-ray diffraction.

The results of the powder X-ray diffraction analysis of this wet crystal are shown in the following.

This wet crystal showed a powder X-ray diffraction pattern having characteristic peaks at interplanar spacings (d) of 5.88, 4.70, 4.35, 3.66 and 3.48 Angstroms in powder X-ray diffraction.

As a result of the analysis of this crystal by high performance liquid chromatography (condition (A)), the enantiomer excess of the crystal was 100% ee.

Example 2

Production Method of (R)-Form

Using the reaction mixture produced according to Reference Example 1, (R)-2-[[[3-methyl-4-(2,2,2-trifluoroethoxy)-2-pyridyl]methyl]sulfinyl]benzimidazole (13.0 g, enantiomer excess 100% ee, containing sulfone form 1.5%) obtained according to Example 1 was dissolved in acetone (100 ml). To the obtained solution was dropwise added water (360 ml), and the mixture was stirred under ice-cooling for 1 hr. The precipitated crystal was separated to give a wet crystal of an (R)-form (yield (amount) after drying: 12.5 g, yield (percentage) after drying: 96.2%) having the following interplanar spacing (d) in powder X-ray diffraction.

The results of the powder X-ray diffraction analysis of this wet crystal are shown in the following.

This wet crystal showed a powder X-ray diffraction pattern having characteristic peaks at interplanar spacings (d) of 8.33, 6.63, 5.86 and 4.82 Angstroms in powder X-ray diffraction. The crystal was analyzed by high performance liquid chromatography (condition (B)), and as a result, the proportion of a sulfone form in the crystal was 0%, and other analogous substances were not present.

Example 3

Production Method of (R)-Form (1) Under a nitrogen stream, 2-[[[3-methyl-4-(2,2,2-trifluoroethoxy)-2-pyridyl]methyl]thio]benzimidazole (4.5 kg, 12.7 mol, containing 1.89 g of water), toluene (22 L), water (25 g, 1.39 mol, total amount of water 1.49 mol) and diethyl (+)-tartrate (0.958 L, 5.60 mol) were mixed. Under a nitrogen stream, titanium(IV) isopropoxide (0.747 L, 2.53 mol) was added to the mixture at 50 to 60° C., and the mixture was stirred at the same temperature for 30 min. Under a nitrogen stream, diisopropylethylamine (0.733 L, 4.44 mol) was added to the obtained mixture at room temperature, cumene hydroperoxide (6.88 L, content 82%, 37.5 mol) was added at −5 to 5° C., and the mixture was stirred at −5 to 5° C. for 1.5 hr to give a reaction mixture.

As a result of the analysis of the reaction mixture by high performance liquid chromatography (condition (B)), 1.87% of a sulfide form and 1.59% of a sulfone form were present as analogous substances in the reaction mixture, and other analogous substances were not present.

(2) To the reaction mixture obtained in the above-mentioned (1) was added 30% aqueous sodium thiosulfate solution (17 L) under a nitrogen stream to decompose the remaining cumene hydroperoxide. The mixture was partitioned and to the obtained organic layer were successively added water (4.5 L), heptane (13.5 L), t-butyl methyl ether (18 L) and heptane (27 L). The mixture stirred at about 10° C. to allow crystallization. The crystal was separated and washed with t-butyl methyl ether-toluene (t-butyl methyl ether:toluene=4:1) (4 L) to give an (R)-form having the following interplanar spacing (d) in powder X-ray diffraction as a wet crystal.

The results of the powder X-ray diffraction analysis of this wet crystal are shown in the following.

This wet crystal showed a powder X-ray diffraction pattern having characteristic peaks at interplanar spacings (d) of 5.88, 4.70, 4.35, 3.66 and 3.48 Angstroms in powder X-ray diffraction. A chart of the powder X-ray diffraction is shown in FIG. 1.

As a result of the analysis of this crystal by high performance liquid chromatography (condition (A)), 0.90% of a sulfone form was present as an analogous substance in the crystal, and a sulfide form and other analogous substances were not present. The enantiomer excess of the (R)-form in the crystal was 100% ee.

(3) Under stirring, a suspension of the wet crystal obtained in the above-mentioned (2) in acetone (20 L) was added dropwise to a mixture of acetone (7 L) and water (34 L), and then water (47 L) was added. The mixture was stirred at about 10° C. and the precipitated crystal was separated, and washed with acetone-water (acetone:water=1:3) (4 L) and water (12 L) to give an (R)-form having the following interplanar spacing (d) in powder X-ray diffraction as a wet crystal.

The results of the powder X-ray diffraction analysis of this wet crystal are shown in the following.

Figure 2:
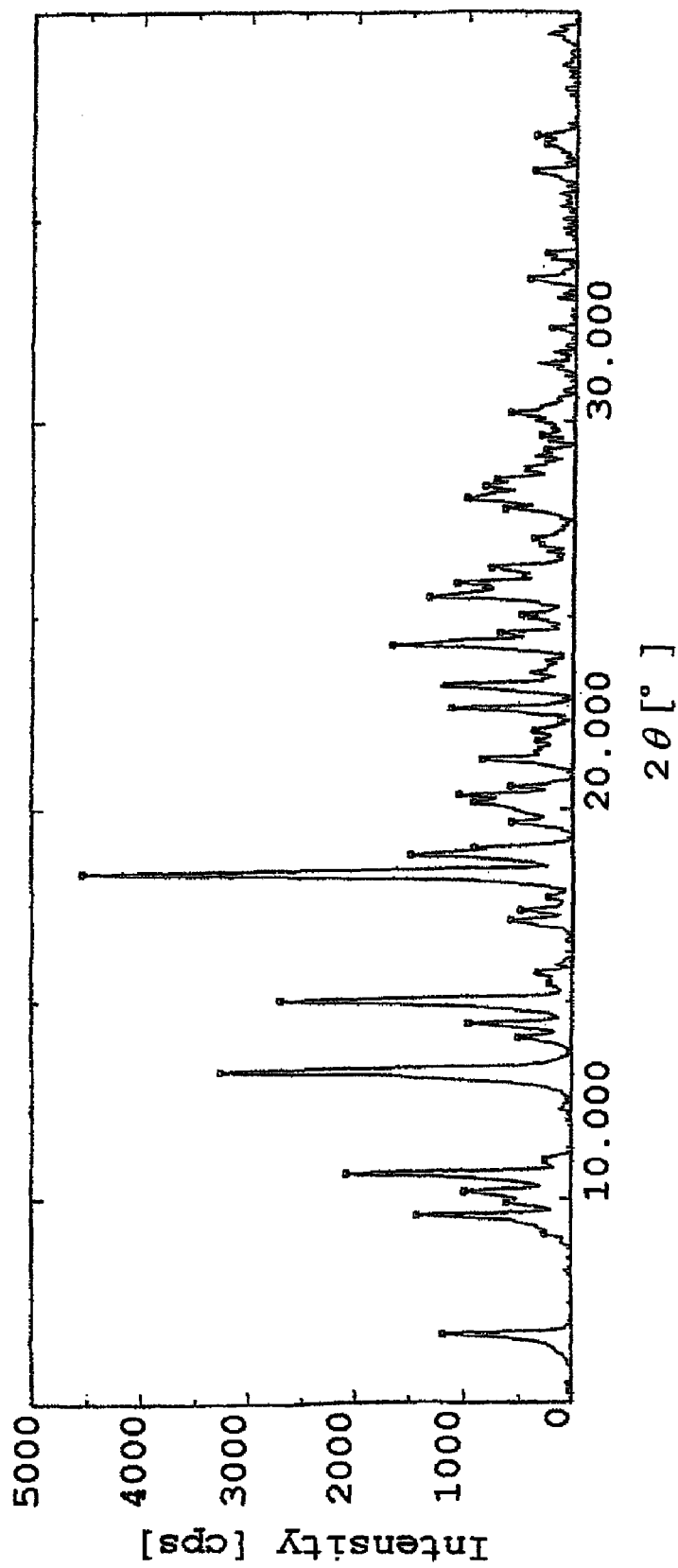
FIG. 2 shows a powder X-ray diffraction chart of the wet crystal of Example 3(3).

This wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 2.

As a result of the analysis of this crystal by high performance liquid chromatography (condition (A)), a sulfone form, a sulfide form and other analogous substance were not present as analogous substances in the crystal. The enantiomer excess of the (R)-form in the crystal was 100% ee.

(4) The wet crystal obtained in the above-mentioned (3) was dissolved in ethyl acetate (45 L) and water (3 L), and then partitioned. A trace amount of an insoluble material in the organic layer was filtered off and triethylamine (0.2 L) was added. The mixture was concentrated under reduced pressure to a liquid amount of about 7 L. To the concentrate were added methanol (2.3 L), about 12.5% aqueous ammonia (23 L) at about 50° C., and t-butyl methyl ether (22 L) at about 50° C. for partitioning. About 12.5% aqueous ammonia (11 L) was added to the organic layer for partitioning (this operation was repeated one more time). The aqueous layers were combined and ethyl acetate (22 L) was added, after which acetic acid was added dropwise under cooling to adjust its pH to about 8. The solution was partitioned and an aqueous layer was extracted with ethyl acetate (11 L). The organic layers were combined and washed with about 20% brine (11 L). Triethylamine (0.2 L) was added and the organic layer was concentrated under reduced pressure. Acetone (5 L) was added to the concentrate and the mixture was concentrated under reduced pressure. The concentrate was dissolved in acetone (9 L) and the solution was added dropwise to a mixture of acetone (4.5 L) and water (22.5 L). Then, water (18 L) was added dropwise to the obtained mixture, and the mixture was stirred at about 10° C. The precipitated crystal was separated and washed successively with cold acetone-water (1:3) (3 L) and water (12 L) to give an (R)-form having the following interplanar spacing (d) in powder X-ray diffraction as a wet crystal.

The results of the powder X-ray diffraction analysis of this wet crystal are shown in the following.

Figure 3:
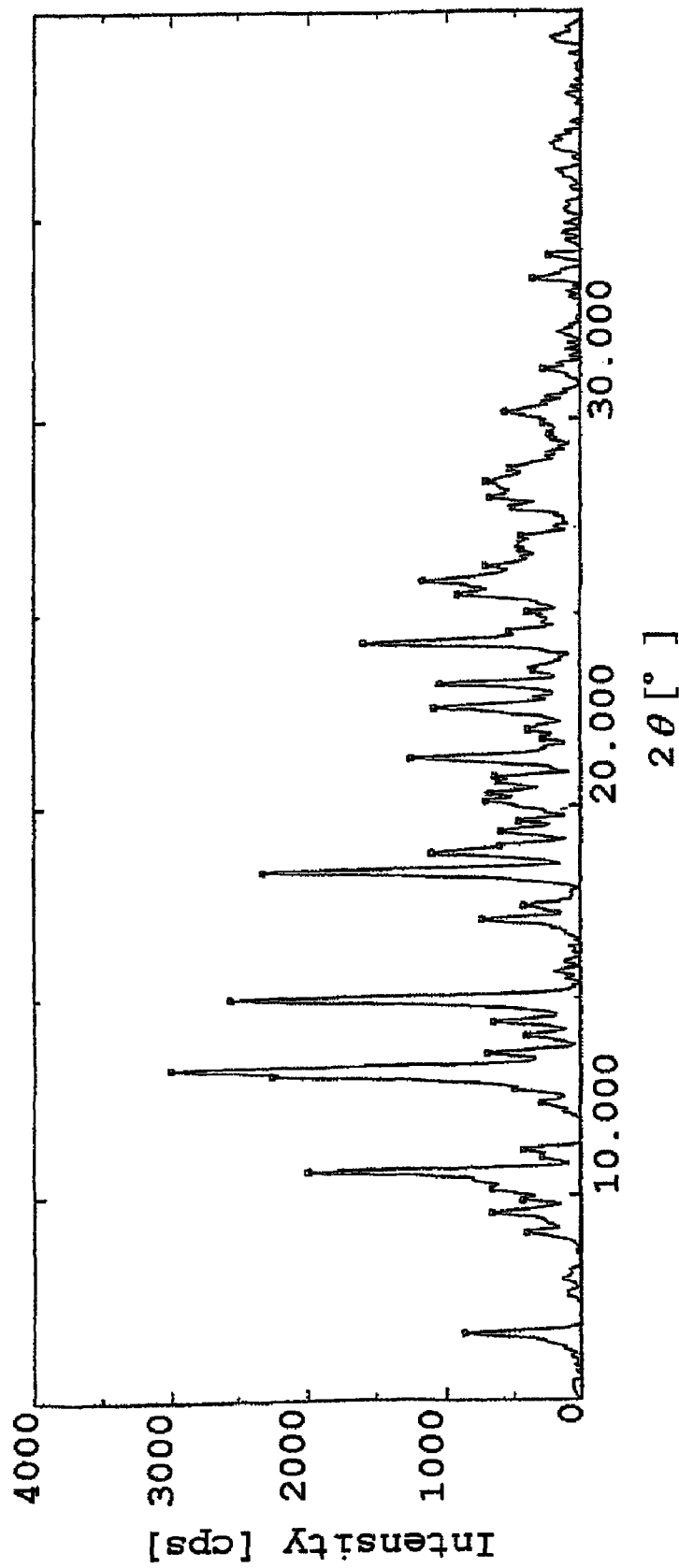
FIG. 3 shows a powder X-ray diffraction chart of the wet crystal of Example 3(4).

This wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 3.

As a result of the analysis of this crystal by high performance liquid chromatography (condition (A)), a sulfone form, a sulfide form and other analogous substance were not present as analogous substances in the crystal. The enantiomer excess of the (R)-form in the crystal was 100% ee.

(5) The wet crystal obtained in the above-mentioned (4) was dissolved in ethyl acetate (32 L). The separated aqueous layer was separated by partitioning and the obtained organic layer was concentrated under reduced pressure to a liquid amount of about 14 L. To the residue were added ethyl acetate (36 L) and active carbon (270 g), and the mixture was stirred and the active carbon was removed by filtration. The filtrate was concentrated under reduced pressure to the liquid amount of about 14 L. Heptane (90 L) was added dropwise at about 40° C. to the residue. After stirring at the same temperature for about 30 min, the crystal was separated and washed with ethyl acetate-heptane (1:8, 6 L) at about 40° C. Drying gave the title compound (3.4 kg).

The results of the powder X-ray diffraction analysis of this crystal are shown in the following.

Figure 4:
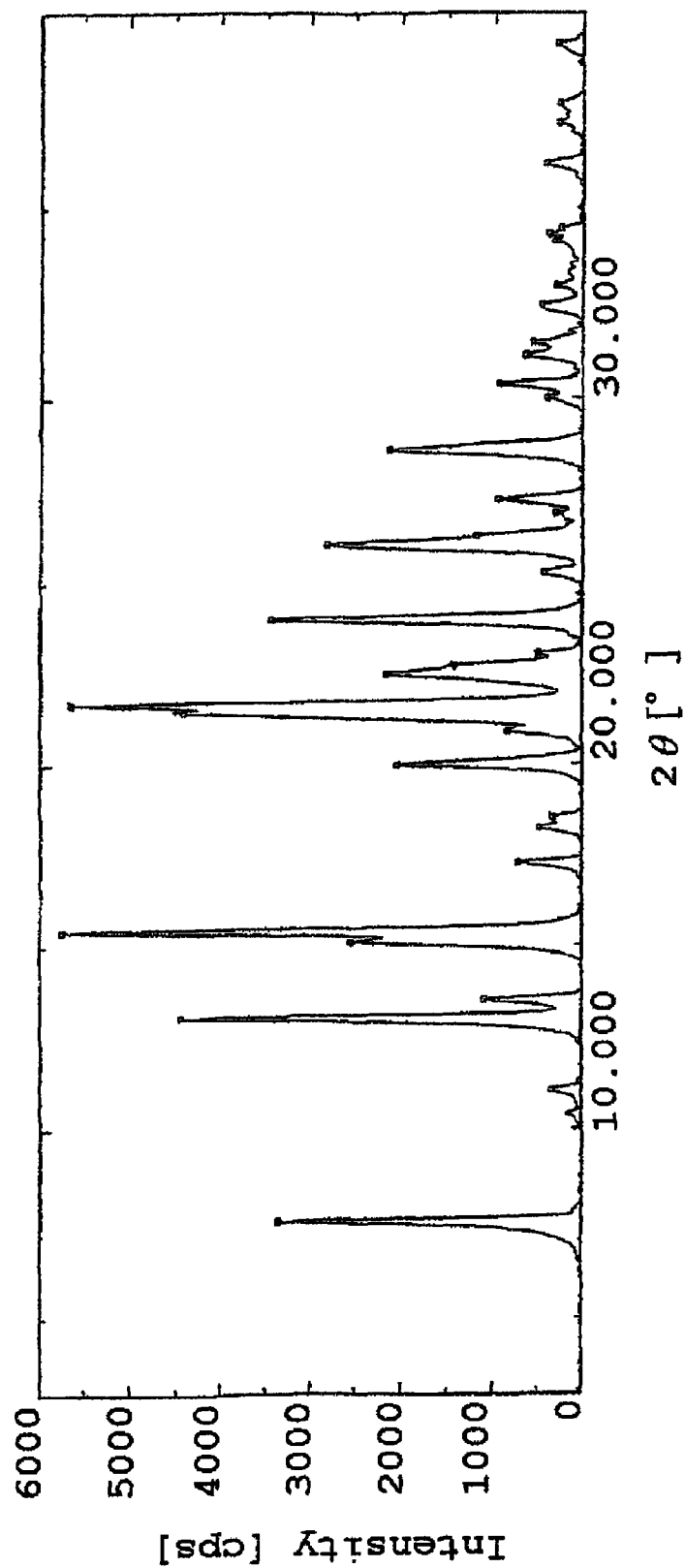
FIG. 4 shows a powder X-ray diffraction chart of the wet crystal of Example 3(5).

The crystal showed a powder X-ray diffraction pattern having characteristic peaks at interplanar spacings (d) of 11.68, 6.77, 5.84, 5.73, 4.43, 4.09, 3.94, 3.89, 3.69, 3.41, 3.11 Angstroms in powder X-ray diffraction. A chart of the powder X-ray diffraction is shown in FIG. 4.

As a result of the analysis of this crystal by high performance liquid chromatography (condition (A)), a sulfone form, a sulfide form and other analogous substance were not present as analogous substances in the crystal. The enantiomer excess of the (R)-form in the crystal was 100% ee.

Example 4

Production Method of (S)-Form (1) Under a nitrogen atmosphere, 2-[[[3-methyl-4-(2,2,2-trifluoroethoxy)-2-pyridyl]methyl]thio]benzimidazole (50.0 g, 0.14 mol, containing 20 mg of water), toluene (250 ml), water (130 mg, 0.0072 mol, total amount of water 0.0083 mol) and diethyl (−)-tartrate (5.31 ml, 0.031 mol) were mixed. Under a nitrogen atmosphere, titanium(IV) isopropoxide (4.14 ml, 0.014 mol) was added to the mixture at 50° C., and the mixture was stirred at 50 to 55° C. for 1 hr. Under a nitrogen atmosphere and under cooling, diisopropylethylamine (8.13 ml, 0.047 mol) was added to the obtained mixture and cumene hydroperoxide (76.50 ml, content 82%, 0.42 mol) was added to the mixture at −10 to 0° C., and the mixture was stirred at −5 to 5° C. for 3.5 hr to give a reaction mixture.

As a result of the analysis of the reaction mixture by high performance liquid chromatography (condition (A)), the enantiomer excess of the (S)-form in the reaction mixture was 96.5% ee.

As a result of the analysis of the reaction mixture by high performance liquid chromatography (condition (B)), 1.90% of a sulfone form and 1.50% of a sulfide form were present as analogous substances in the reaction mixture, and other analogous substances were not present.

(2) To the reaction mixture obtained in the above-mentioned (1) was added 30% aqueous sodium thiosulfate solution (180 ml) under a nitrogen stream to decompose the remaining cumene hydroperoxide. After partitioning, to the obtained organic layer were added successively water (50 ml), heptane (150 ml), t-butyl methyl ether (200 ml) and heptane (300 ml) to allow crystallization. The crystal was separated and washed with t-butyl methyl ether-toluene (t-butyl methyl ether:toluene=4:1) (45 ml) to give an (S)-form having the following interplanar spacing (d) in powder X-ray diffraction as a wet crystal.

The results of the powder X-ray diffraction analysis of this wet crystal are shown in the following.

Figure 5:
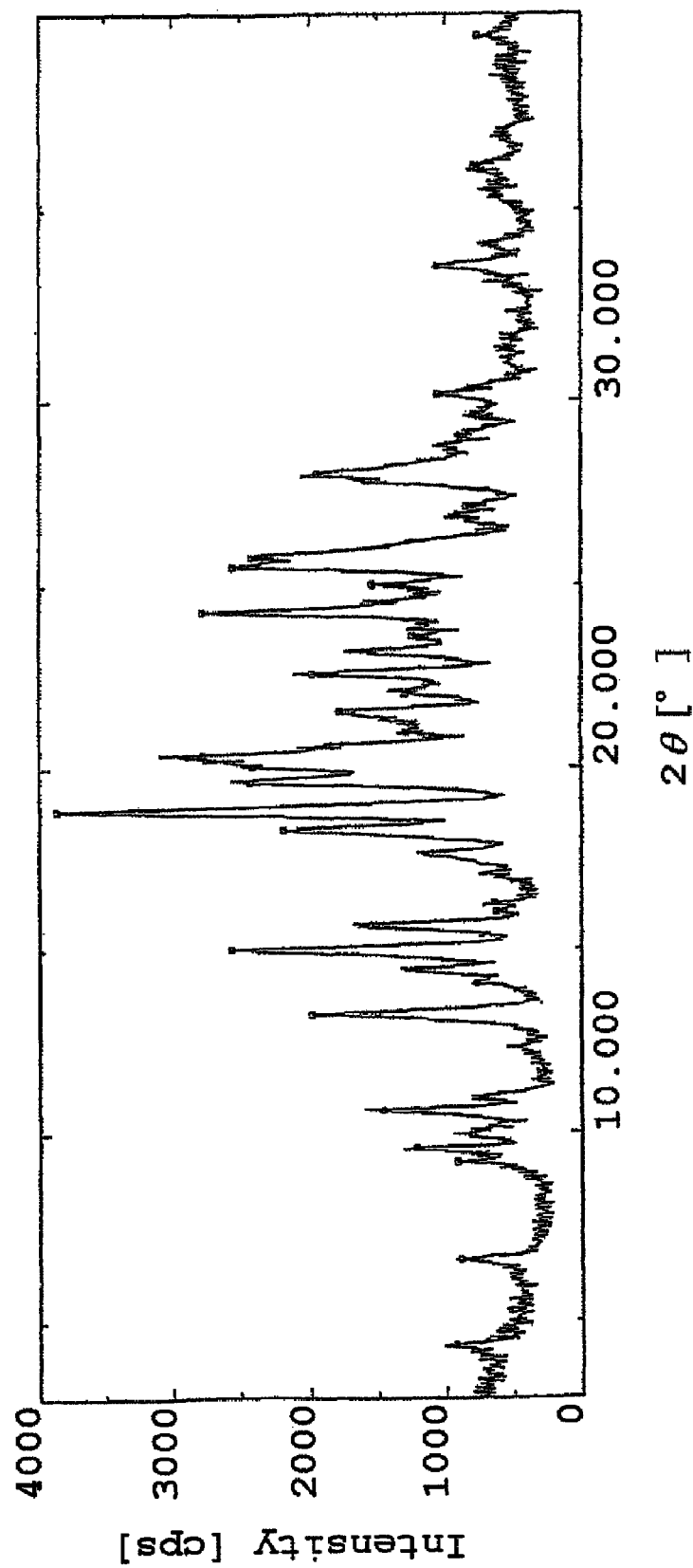
FIG. 5 shows a powder X-ray diffraction chart of the wet crystal of Example 4(2).

This wet crystal showed a powder X-ray diffraction pattern having characteristic peaks at interplanar spacings (d) of 5.88, 4.70, 4.35, 3.66 and 3.48 Angstroms in powder X-ray diffraction. A chart of the powder X-ray diffraction is shown in FIG. 5.

As a result of the analysis of this crystal by high performance liquid chromatography (condition (A)), the enantiomer excess of the crystal was 100% ee.

As a result of the analysis of this crystal by high performance liquid chromatography (condition (B)), 0.72% of a sulfone form was present as an analogous substance in the crystal, and a sulfide form and other analogous substances were not present.

(3) A suspension of the wet crystal obtained in the above-mentioned (2) in acetone (220 ml) was added dropwise to a mixture of acetone (75 ml) and water (370 ml), and water (520 ml) was added. The precipitated crystal was separated and washed with acetone-water (acetone:water=1:3) (44 ml) and water (130 ml) to give an (S)-form having the following interplanar spacing (d) in powder X-ray diffraction as a wet crystal.

Figure 6:
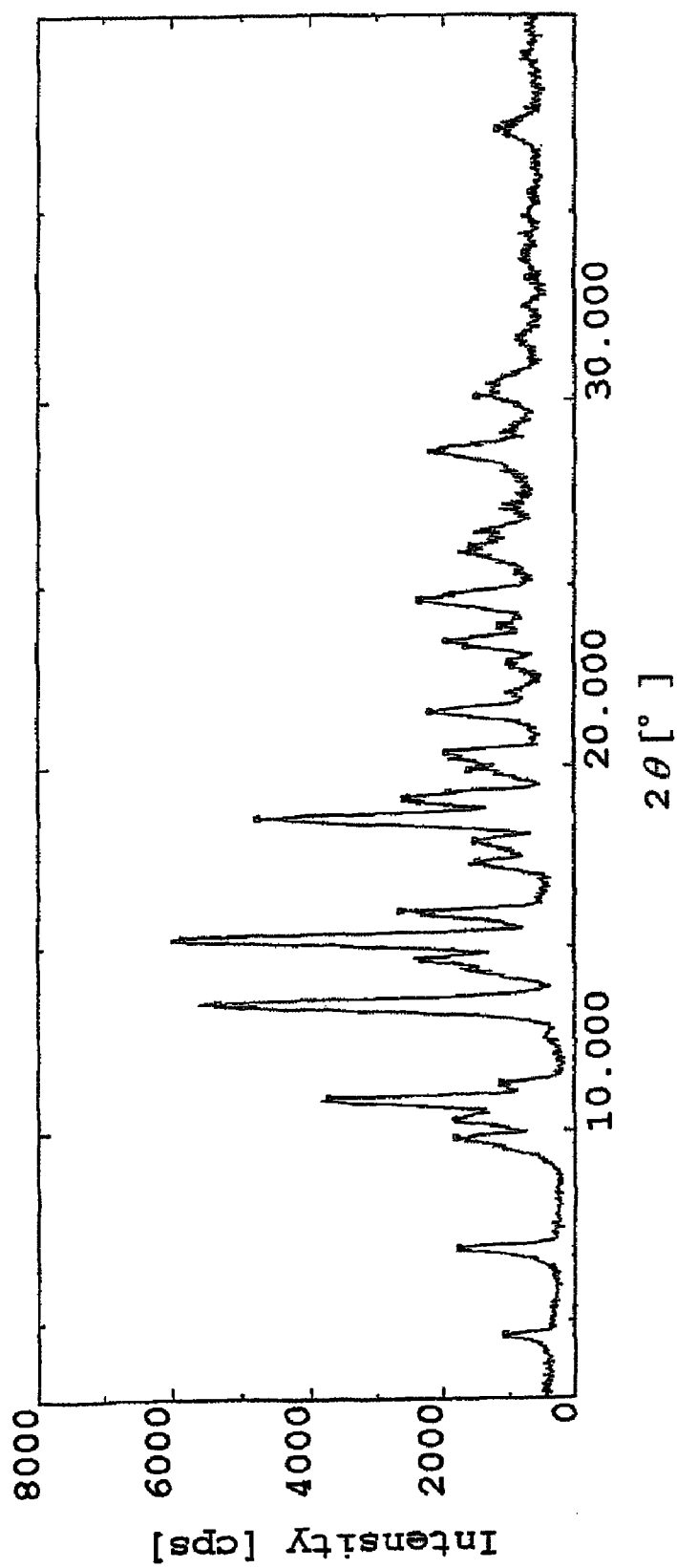
FIG. 6 shows a powder X-ray diffraction chart of the wet crystal of Example 4(3).

As a result of the powder X-ray diffraction analysis of this wet crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 6.

As a result of the analysis of this crystal by high performance liquid chromatography (condition (A)), the enantiomer excess of the crystal was 100% ee.

As a result of the analysis of this crystal by high performance liquid chromatography (condition (B)), a sulfone form, a sulfide form and other analogous substance were not present as analogous substances in the crystal.

Example 5

Production Method of (S)-Form

Figure 7:
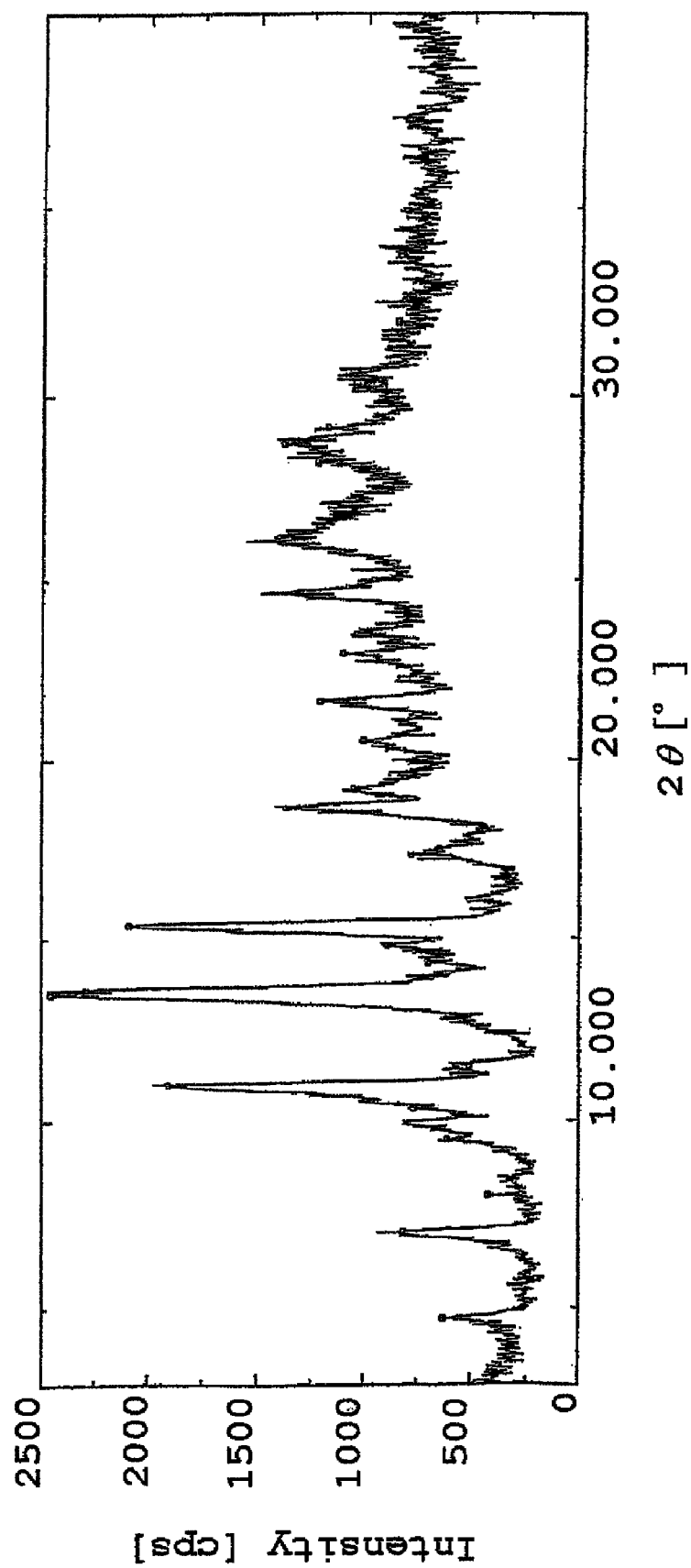
FIG. 7 shows a powder X-ray diffraction chart of the wet crystal (starting material) of Example 5.

A wet crystal (containing 35.37 g of the title compound, analogous substance content: 0%, enantiomer excess: 100% ee, powder X-ray diffraction chart: see FIG. 7) obtained according to Example 4 was dissolved in ethyl acetate (340 ml). The separated aqueous layer was separated by partitioning and the obtained organic layer was concentrated under reduced pressure until the liquid amount became about 100 ml. Ethyl acetate (400 ml) and active carbon (3 g) were added to the residue, and after stirring, active carbon was removed by filtration. The filtrate was concentrated under reduced pressure until the liquid amount became about 100 ml. Heptane (1000 ml) was added dropwise to the residue at about 40° C. The mixture was stirred at the same temperature for about 30 min and the crystal was separated and washed with ethyl acetate-heptane (1:8, 63 ml) at about 40° C. Drying gave 35.08 g of the title compound (yield: 99.2%).

The results of the powder X-ray diffraction analysis of this crystal are shown in the following.

Figure 8:
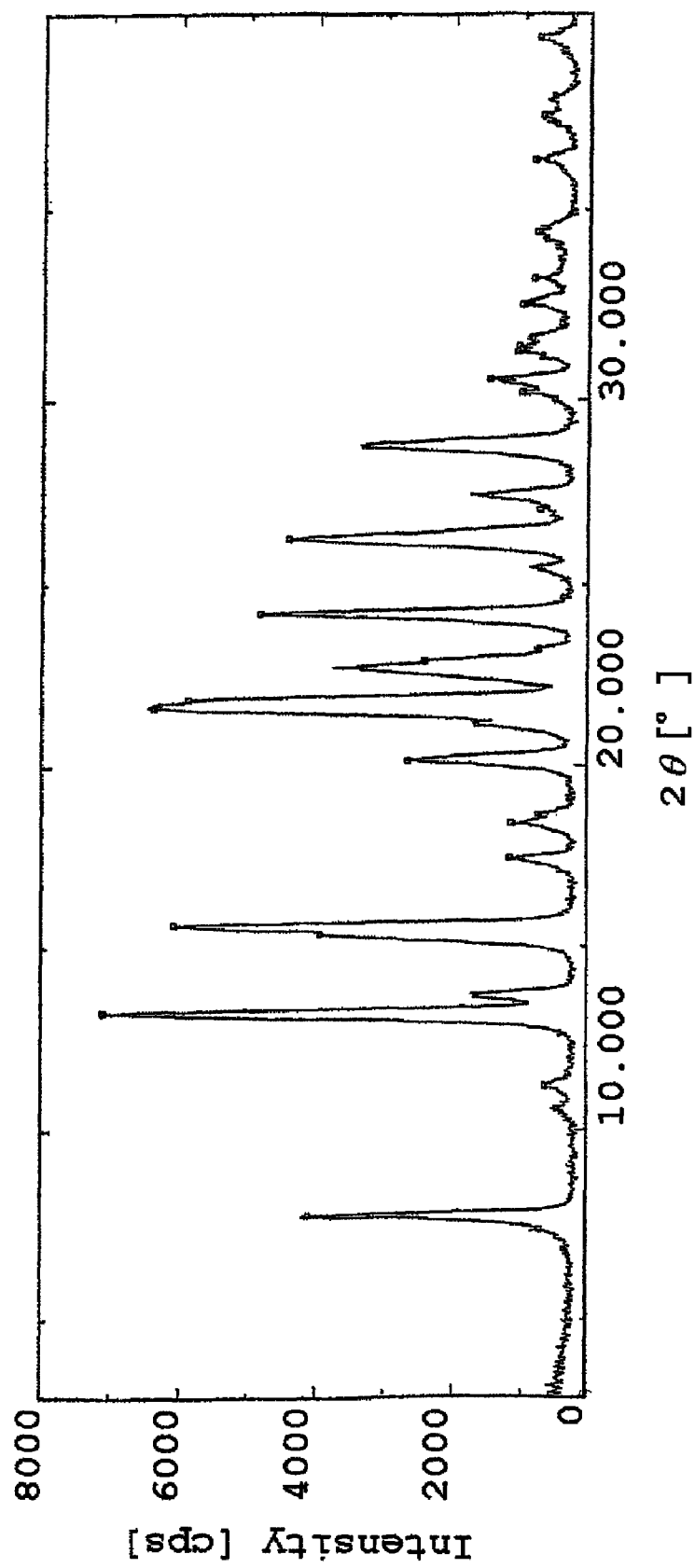
FIG. 8 shows a powder X-ray diffraction chart of the wet crystal (objective substance) of Example 5.

The crystal showed a powder X-ray diffraction analysis pattern having characteristic peaks at interplanar spacings (d) of 11.68, 6.77, 5.84, 5.73, 4.43, 4.09, 3.94, 3.89, 3.69, 3.41 and 3.11 Angstroms in powder X-ray diffraction. A chart of the powder X-ray diffraction is shown in FIG. 8.

As a result of the analysis of this crystal by high performance liquid chromatography (condition (A)), a sulfone form, a sulfide form and other analogous substance were not present as analogous substances in the crystal. The enantiomer excess of the (R)-form in the crystal was 100% ee.

Reference Example 2

Production Method of Solution Containing (R)-2-[[[3-methyl-4-(2,2,2-trifluoroethoxy)-2-pyridyl]methyl]sulfinyl]benzimidazole by Asymmetric Oxidization 2-[[[3-Methyl-4-(2,2,2-trifluoroethoxy)-2-pyridyl]methyl]thio]benzimidazole (30.0 g, 0.085 mol, containing 31 mg of water), toluene (150 mL), water (59 mg, 0.0033 mol, total amount of water 0.0050 mol) and diethyl (+)-tartrate (3.19 mL, 0.019 mol) were mixed and heated to 50 to 55° C. Titanium(IV) isopropoxide (2.49 mL, 0.0085 mol) was added to the mixture under a nitrogen atmosphere, and the mixture was stirred at 50 to 55° C. for 30 min. Under a nitrogen atmosphere and under cooling, diisopropylethylamine (4.88 mL, 0.028 mol) was added to the obtained mixture and cumene hydroperoxide (46.0 mL, 0.26 mol) was added at −5 to 5° C. The mixture was stirred at −5 to 5° C. for 5.5 hr to allow reaction.

As a result of the analysis of the reaction mixture by high performance liquid chromatography (condition (B)), 2.3% of a sulfide form and 2.0% of a sulfone form were present as analogous substances in the reaction mixture, and other analogous substances were not present.

Reference Example 3

Purification method of (R)-2-[[[3-methyl-4-(2,2,2-trifluoroethoxy)-2-pyridyl]methyl]sulfinyl]benzimidazole To the reaction mixture obtained in the above-mentioned Reference Example 2 was added 25% aqueous sodium thiosulfate solution (81 g) under a nitrogen stream to decompose the residual cumene hydroperoxide, and the mixture was concentrated under reduced pressure until the liquid amount became about 150 mL. While maintaining at 0 to 10° C., heptane-t-butyl methyl ether (heptane:t-butyl methyl ether=1:1) (120 mL) was added dropwise and then heptane (420 mL) was added dropwise. The precipitated crystal was separated and washed with cold heptane-t-butyl methyl ether (heptane:t-butyl methyl ether=1:1) (60 mL) to give 67.2 g of a wet crystal.

As a result of the analysis of this crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 98.2% ee.

As a result of the analysis of this crystal by high performance liquid chromatography (condition (B)), 0.85% of a sulfide form and 1.7% of a sulfone form were present as analogous substances in the crystal, and other analogous substances were not present.

Example 6

The wet crystal (3.00 g) obtained in the above-mentioned Reference Example 3 was suspended in acetone (10 mL) and water (40 mL) was added dropwise. After stirring for 6 hr, the precipitated crystal was separated.

Figure 9:
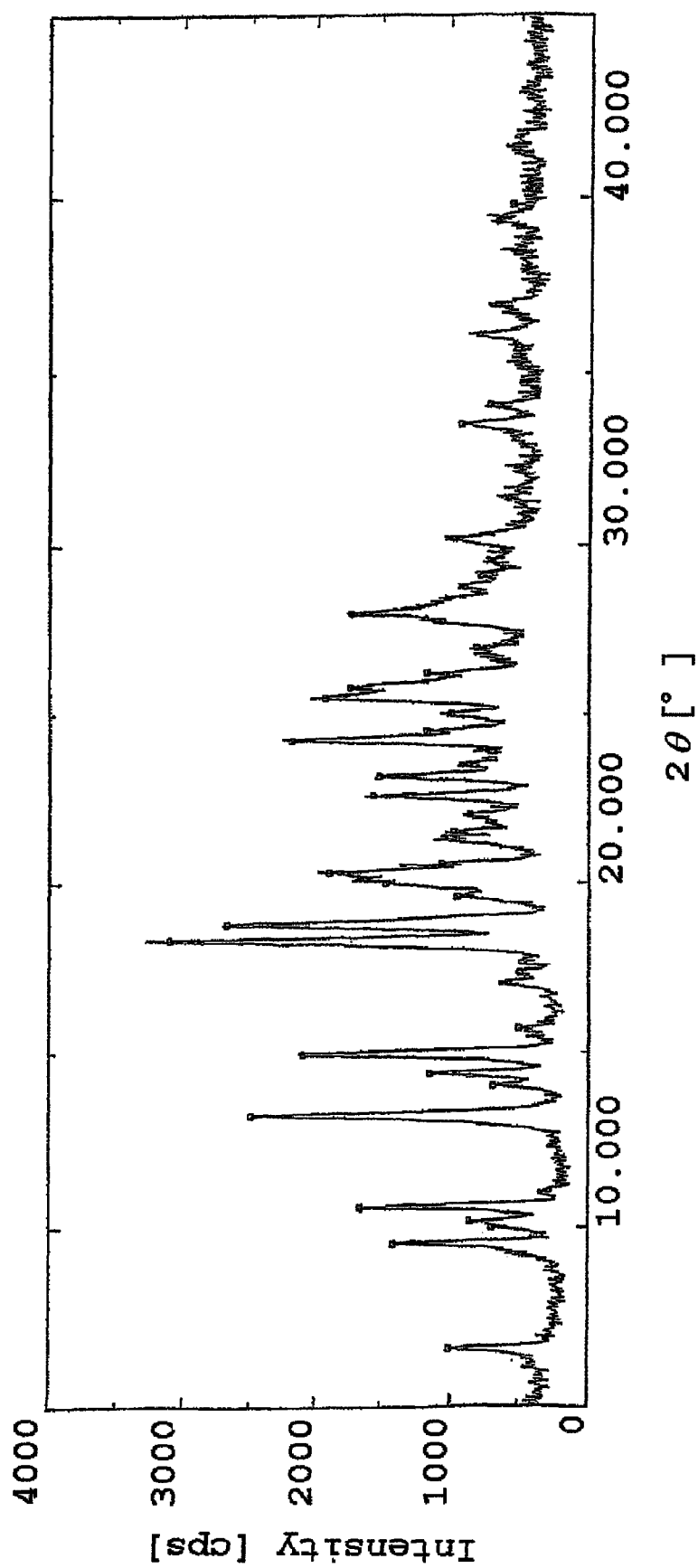
FIG. 9 shows a powder X-ray diffraction chart of the wet crystal of Example 6.

As a result of the powder X-ray diffraction analysis of this wet crystal, this wet crystal showed a powder X-ray diffraction analysis pattern having characteristic peaks at interplanar spacings (d) of 8.33, 6.63, 5.86 and 4.82 Angstroms in powder X-ray diffraction. A chart of the powder X-ray diffraction is shown in FIG. 9.

As a result of the analysis of this wet crystal by high performance liquid chromatography (condition (B)), 0.61% of a sulfide form and 0.56% of a sulfone form were present as analogous substances in the crystal, and other analogous substances were not present.

Example 7

The wet crystal obtained in the above-mentioned Example 6 was dried.

Figure 10:
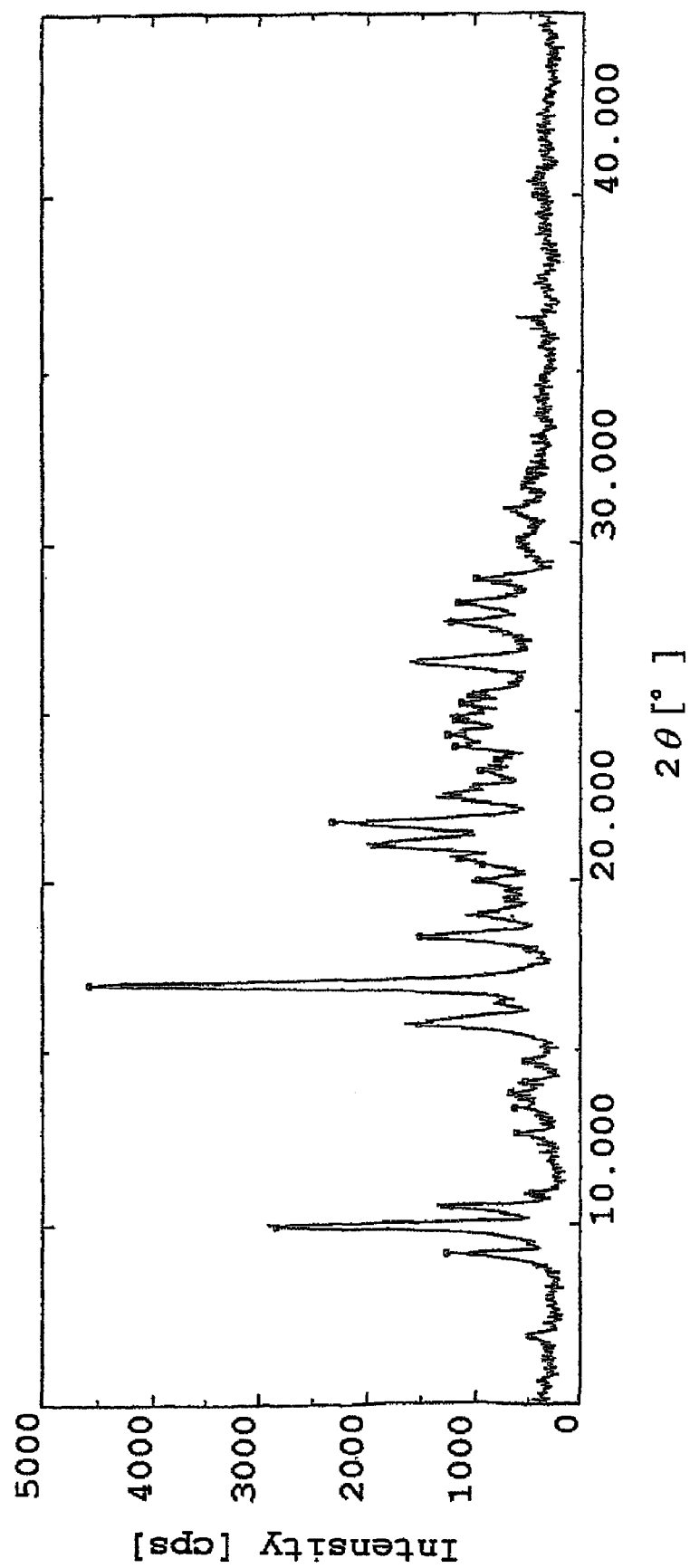
FIG. 10 shows a powder X-ray diffraction chart of the wet crystal of Example 7.

As a result of the powder X-ray diffraction analysis of this crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 10.

As a result of the analysis of this crystal by high performance liquid chromatography (condition (A)), an enantiomer excess of (R)-2-[[[3-methyl-4-(2,2,2-trifluoroethoxy)-2-pyridyl]methyl]sulfinyl]benzimidazole in the crystal was 99.8% ee.

Example 8

The wet crystal (3.00 g) obtained in the above-mentioned Reference Example 3 was suspended in tetrahydrofuran (10 mL) and water (80 mL) was added dropwise. After stirring for 5 hr, the precipitated crystal was separated.

Figure 11:
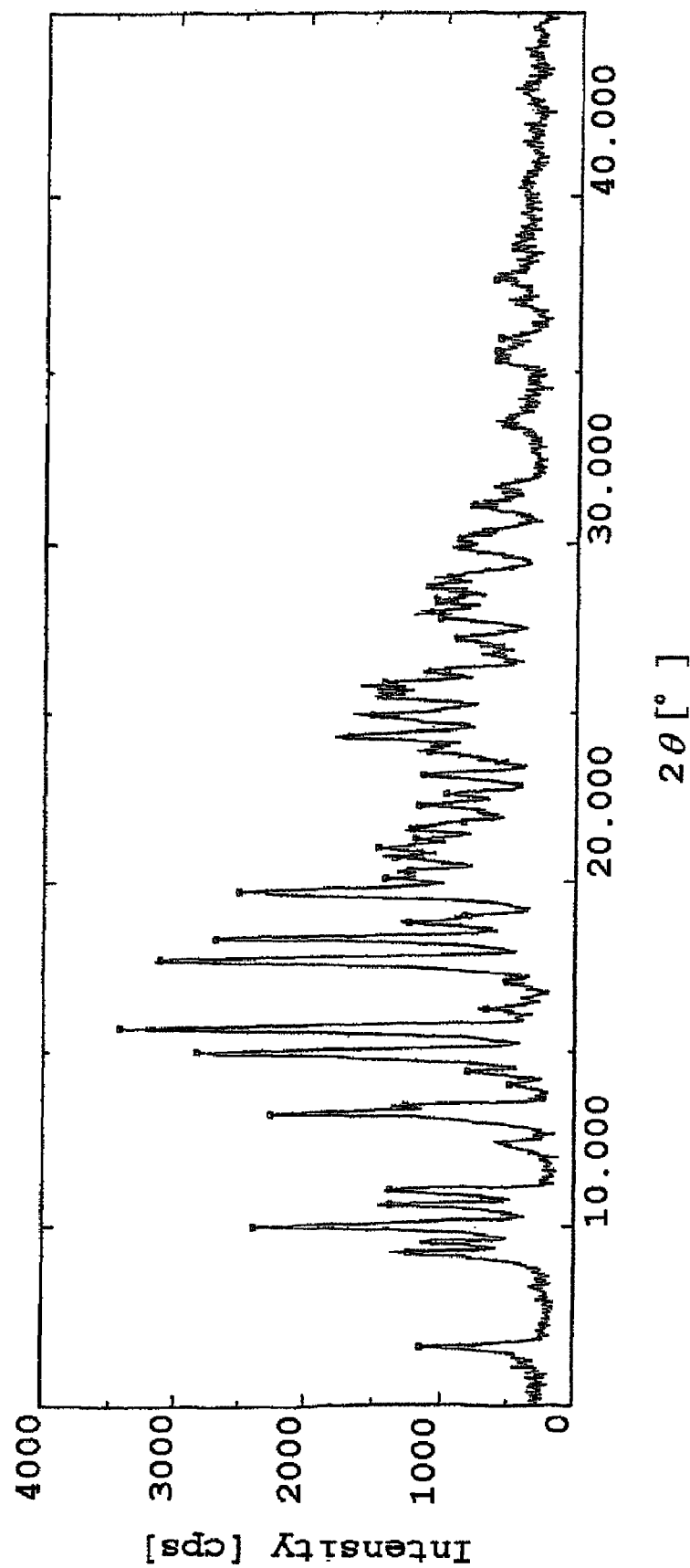
FIG. 11 shows a powder X-ray diffraction chart of the wet crystal of Example 8.

As a result of the powder X-ray diffraction analysis of this wet crystal, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 11.

As a result of the analysis of this wet crystal by high performance liquid chromatography (condition (B)), 0.63% of a sulfide form and 0.50% of a sulfone form were present as analogous substances in the crystal, and other analogous substances were not present.

Example 9

The wet crystal obtained in the above-mentioned Example 8 was dried.

Figure 12:
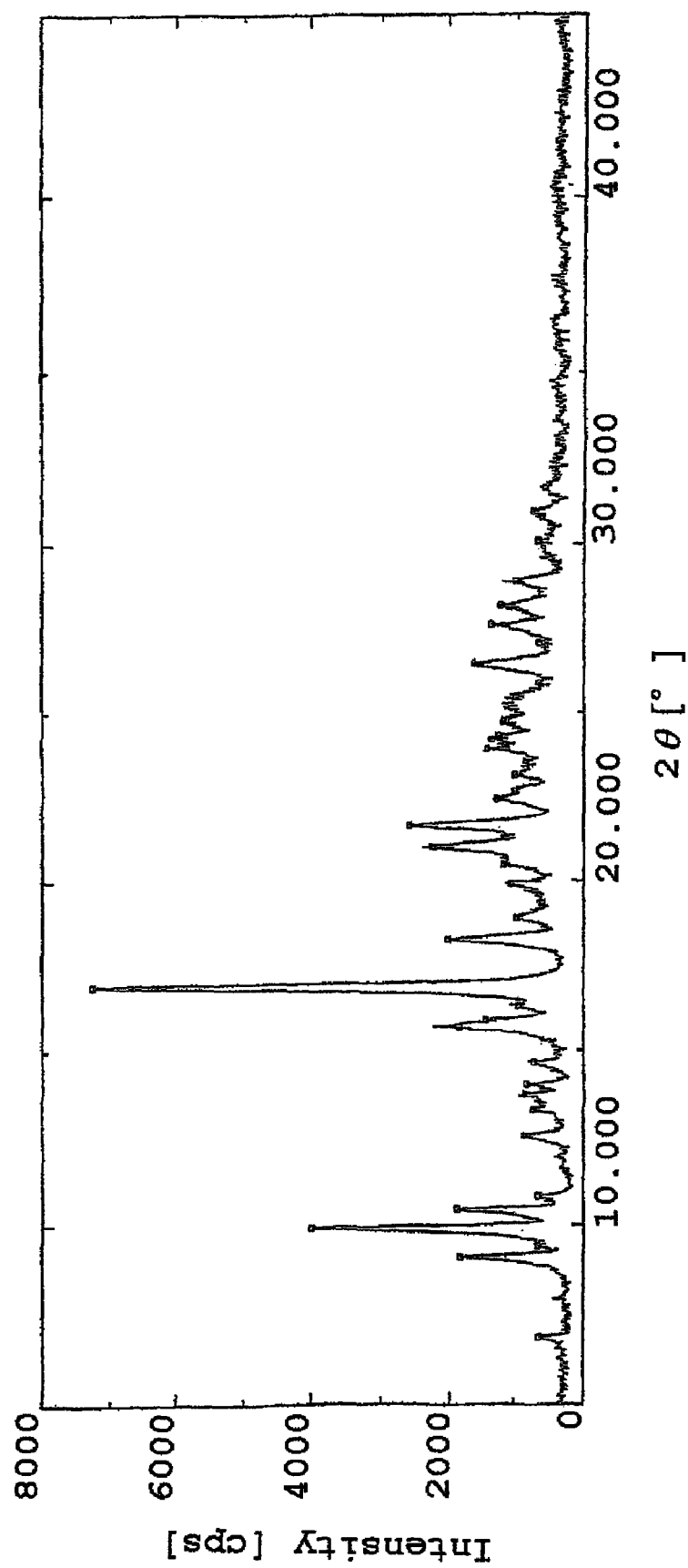
FIG. 12 shows a powder X-ray diffraction chart of the wet crystal of Example 9.

As a result of the powder X-ray diffraction analysis of this crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 12.

As a result of the analysis of this crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 99.8% ee.

Example 10

The wet crystal (3.00 g) obtained in the above-mentioned Reference Example 3 was suspended in isopropanol (10 mL) and water (40 mL) was added dropwise. After stirring for 5 hr, the precipitated crystal was separated.

Figure 13:
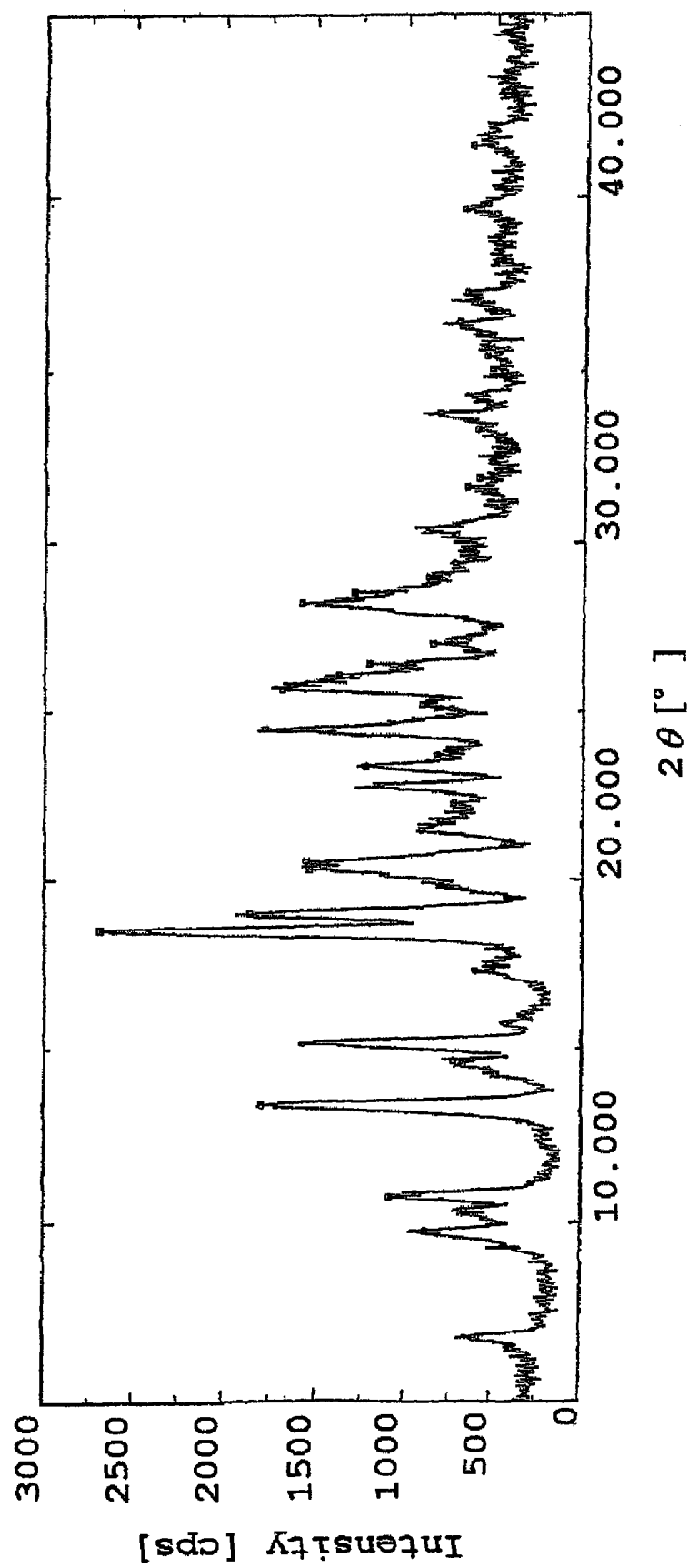
FIG. 13 shows a powder X-ray diffraction chart of the wet crystal of Example 10.

As a result of the powder X-ray diffraction analysis of this wet crystal, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 13.

As a result of the analysis of this wet crystal by high performance liquid chromatography (condition (B)), 0.68% of a sulfide form and 0.64% of a sulfone form were present as analogous substances in the crystal, and other analogous substances were not present.

Example 11

The wet crystal obtained in the above-mentioned Example 10 was dried.

Figure 14:
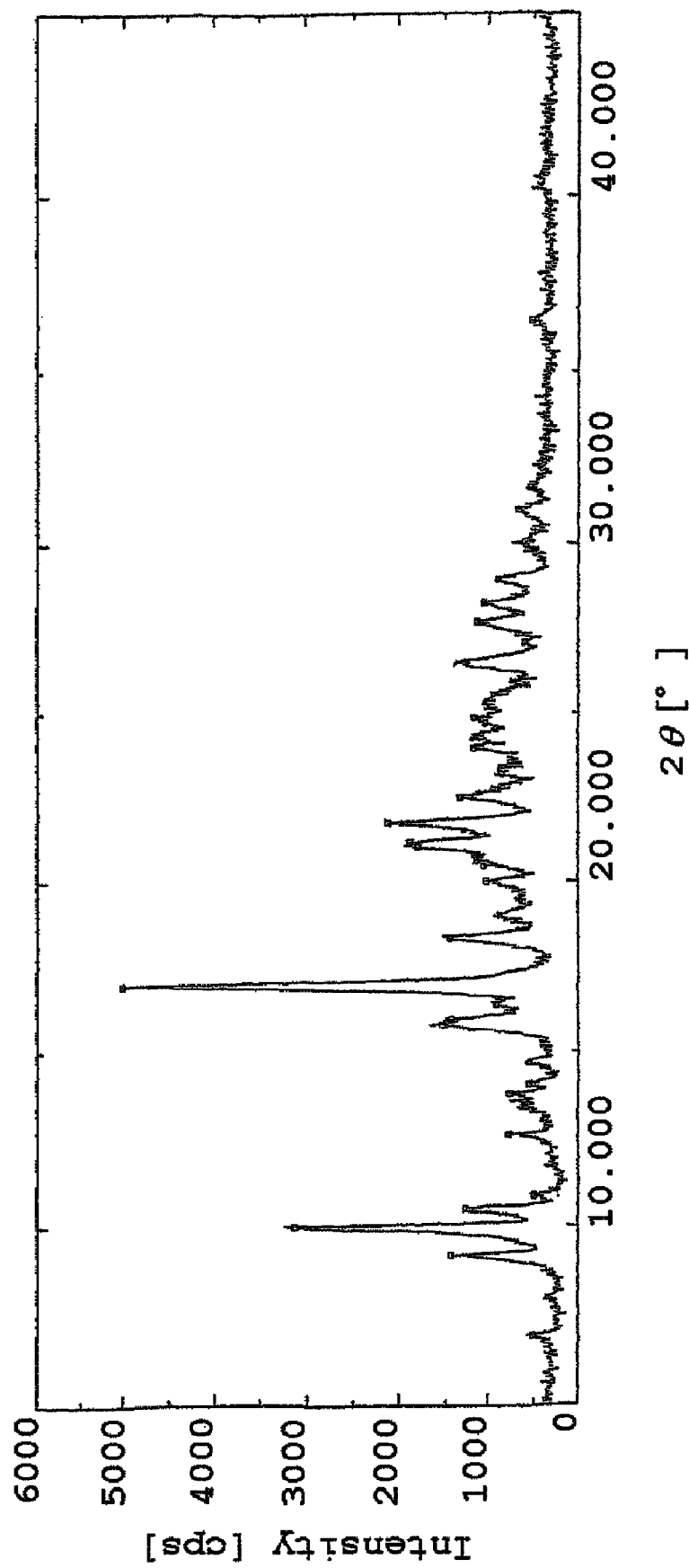
FIG. 14 shows a powder X-ray diffraction chart of the wet crystal of Example 11.

As a result of the powder X-ray diffraction analysis of this crystal, this crystal showed a powder X-ray diffraction analysis pattern having characteristic peaks at interplanar spacings (d) of 8.33, 6.63, 5.86 and 4.82 Angstroms in powder X-ray diffraction. A chart of the powder X-ray diffraction is shown in FIG. 14.

As a result of the analysis of this crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 99.7% ee.

Example 12

The wet crystal (3.00 g) obtained in the above-mentioned Reference Example 3 was suspended in N,N-dimethylformamide (10 mL) and water (40 mL) was added dropwise. After stirring for 5 hr, the precipitated crystal was separated.

Figure 15:
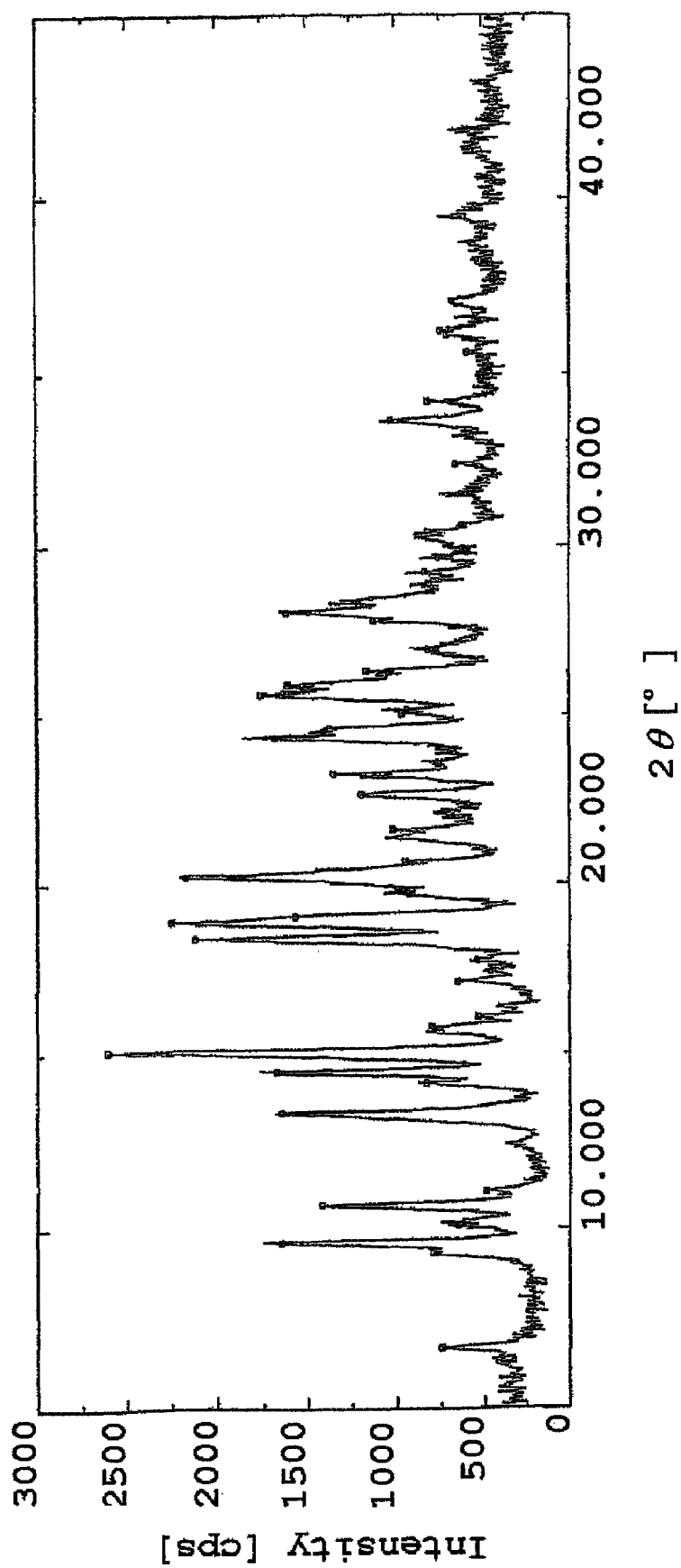
FIG. 15 shows a powder X-ray diffraction chart of the wet crystal of Example 12.

As a result of the powder X-ray diffraction analysis of this wet crystal, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 15.

As a result of the analysis of this wet crystal by high performance liquid chromatography (condition (B)), 0.70% of a sulfide form and 0.41% of a sulfone form were present as analogous substances in the crystal, and other analogous substances were not present.

Example 13

The wet crystal obtained in the above-mentioned Example 12 was dried.

Figure 16:
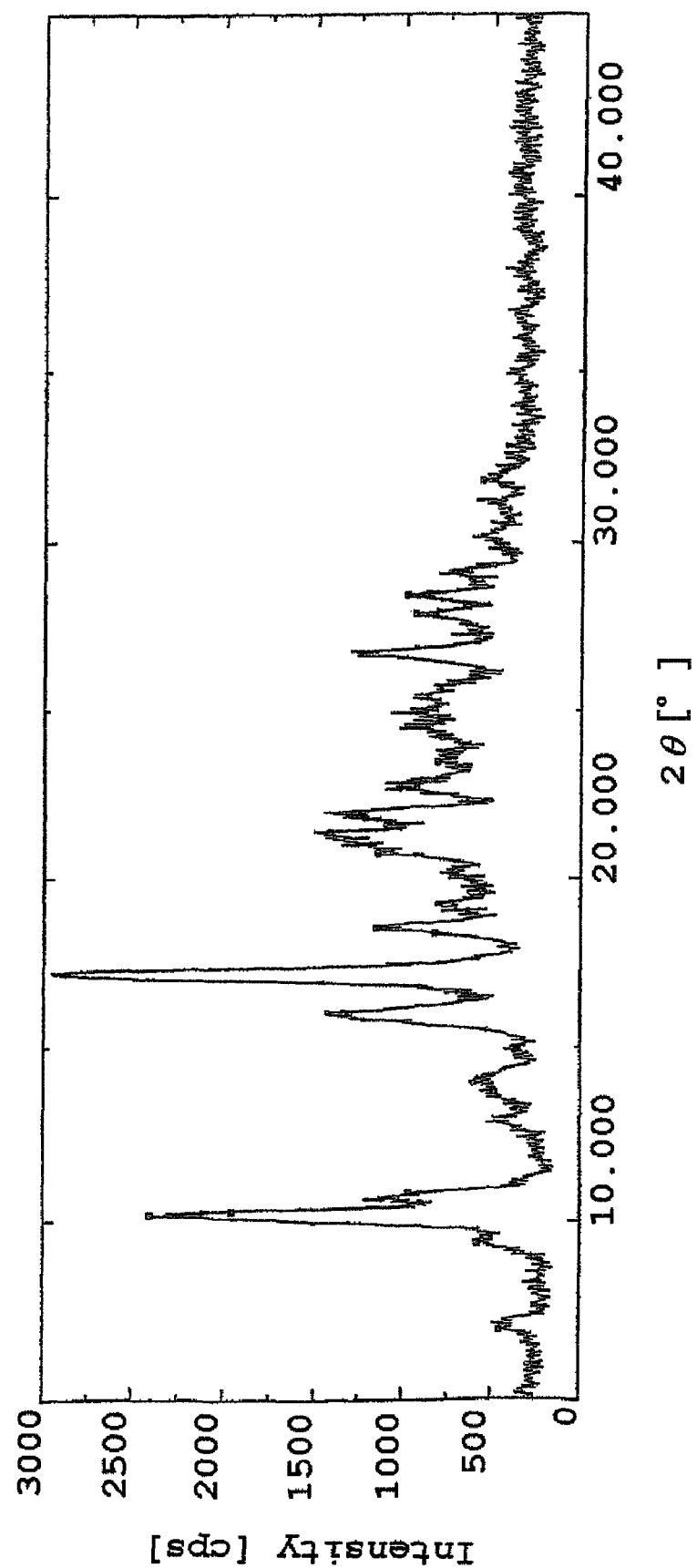
FIG. 16 shows a powder X-ray diffraction chart of the crystal of Example 13.

As a result of the powder X-ray diffraction analysis of this crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 16.

As a result of the analysis of this crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 99.7% ee.

Example 14

The wet crystal (3.00 g) obtained in the above-mentioned Reference Example 3 was suspended in methanol (10 mL) and water (40 mL) was added dropwise. After stirring for 6 hr, the precipitated crystal was separated.

Figure 17:
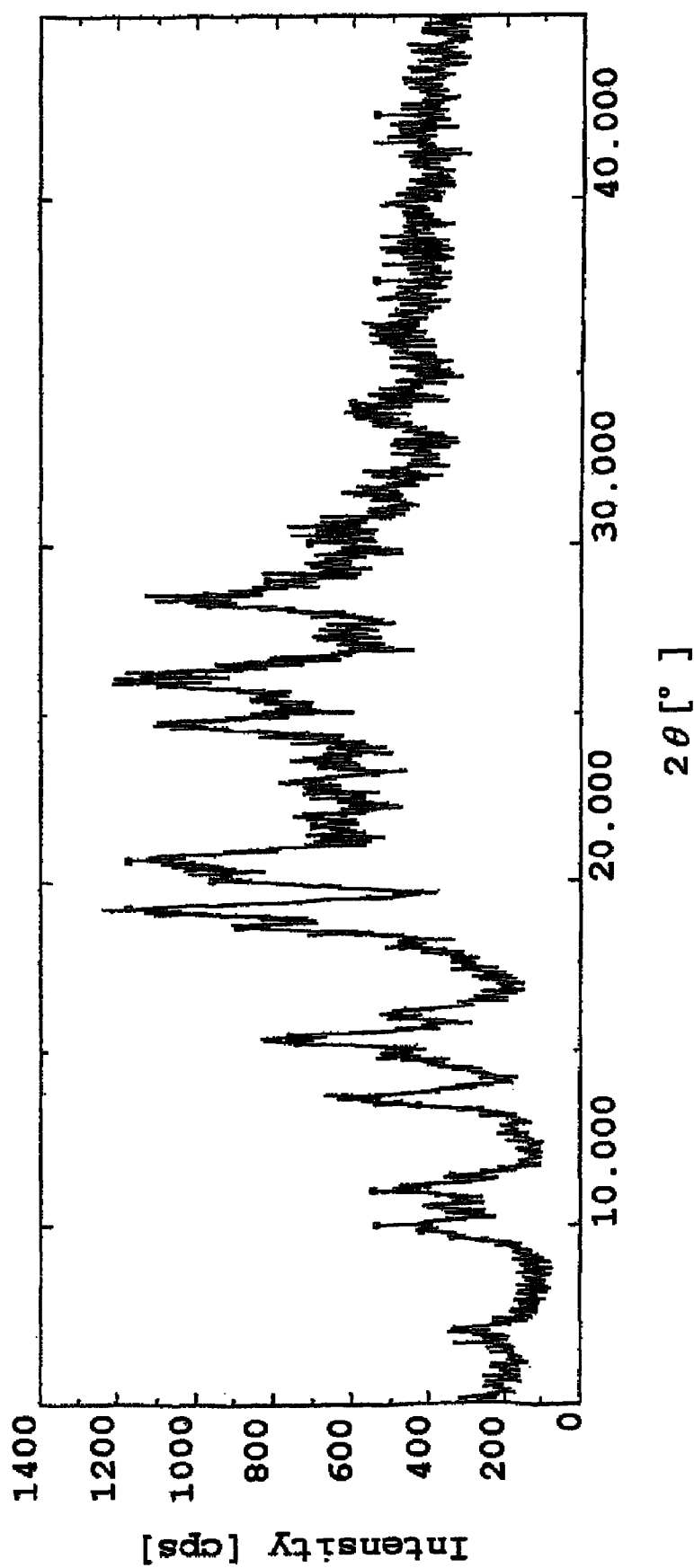
FIG. 17 shows a powder X-ray diffraction chart of the wet crystal of Example 14.

As a result of the powder X-ray diffraction analysis of this wet crystal, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 17.

As a result of the analysis of this wet crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 99.5% ee.

As a result of the analysis of this wet crystal by high performance liquid chromatography (condition (B)), 0.72% of a sulfide form and 0.60% of a sulfone form were present as analogous substances in the crystal, and other analogous substances were not present.

Example 15

The wet crystal obtained in the above-mentioned Example 14 was dried.

Figure 18:
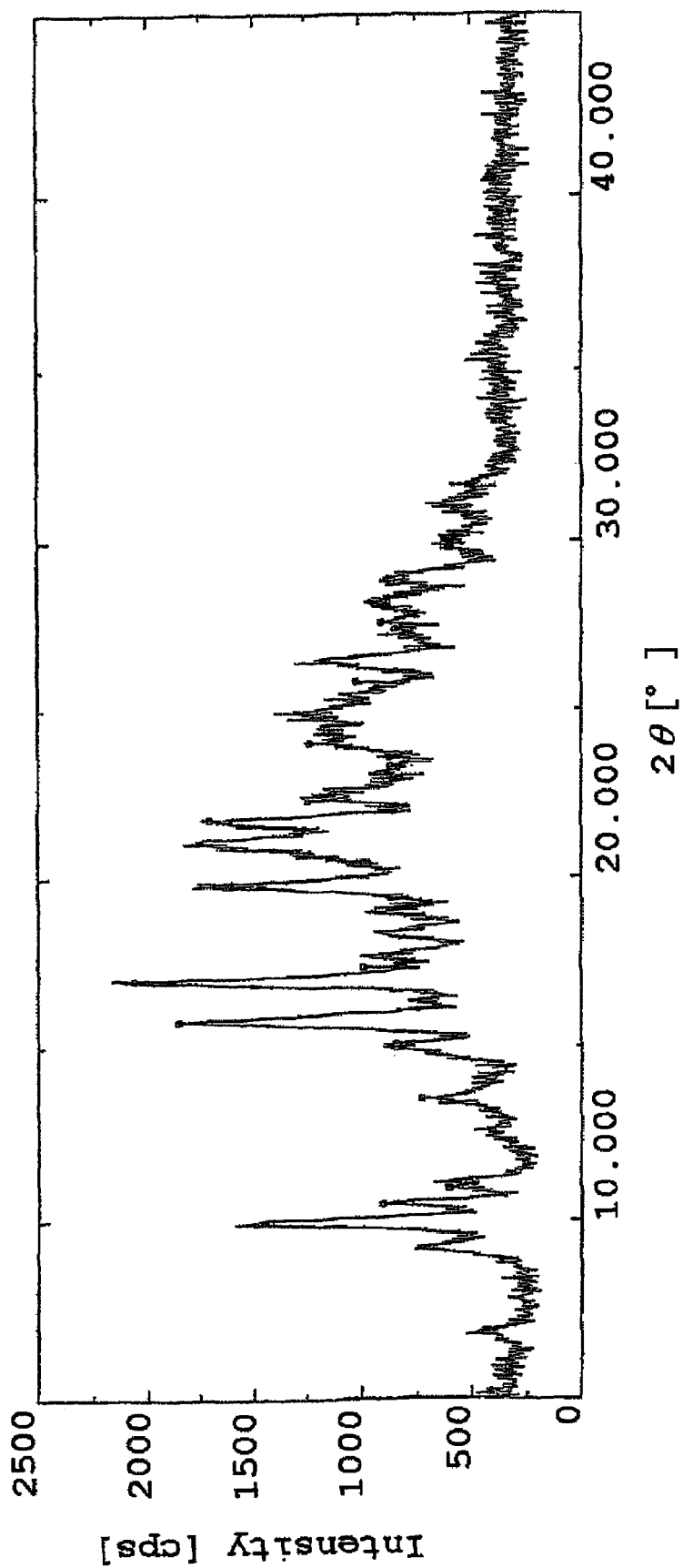
FIG. 18 shows a powder X-ray diffraction chart of the crystal of Example 15.

As a result of the powder X-ray diffraction analysis of this crystal, this crystal showed a powder X-ray diffraction analysis pattern having characteristic peaks at interplanar spacings (d) of 8.33, 6.63, 5.86 and 4.82 Angstroms in powder X-ray diffraction. A chart of the powder X-ray diffraction is shown in FIG. 18.

Example 16

The wet crystal (3.00 g) obtained in the above-mentioned Reference Example 3 was suspended in ethanol (10 mL) and water (40 mL) was added dropwise. After stirring for 6 hr, the precipitated crystal was separated.

Figure 19:
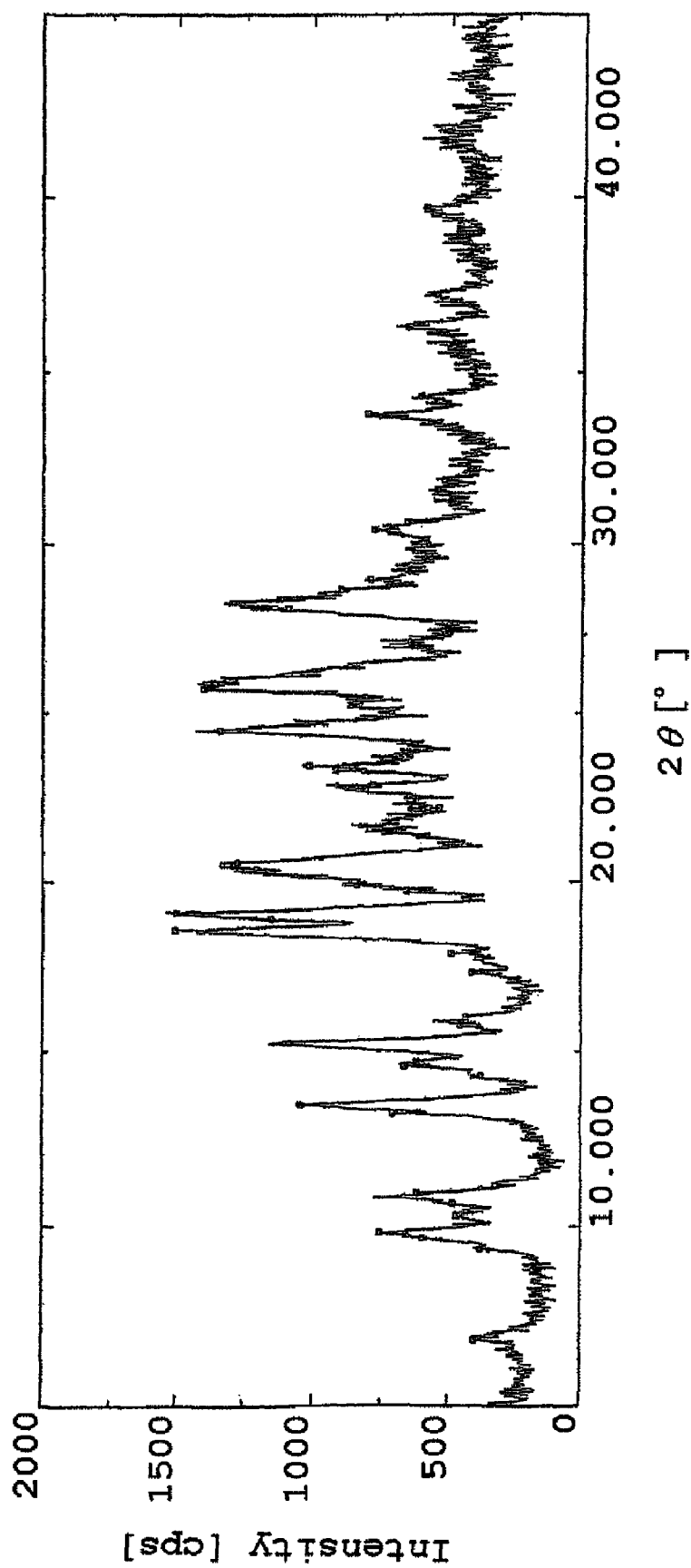
FIG. 19 shows a powder X-ray diffraction chart of the wet crystal of Example 16.

As a result of the powder X-ray diffraction analysis of this wet crystals, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 19.

As a result of the analysis of this wet crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 100% ee.

As a result of the analysis of this wet crystal by high performance liquid chromatography (condition (B)), 0.68% of a sulfide form and 0.63% of a sulfone form were present as analogous substances in the crystal, and other analogous substances were not present.

Example 17

The wet crystal obtained in the above-mentioned Example 16 was dried.

Figure 20:
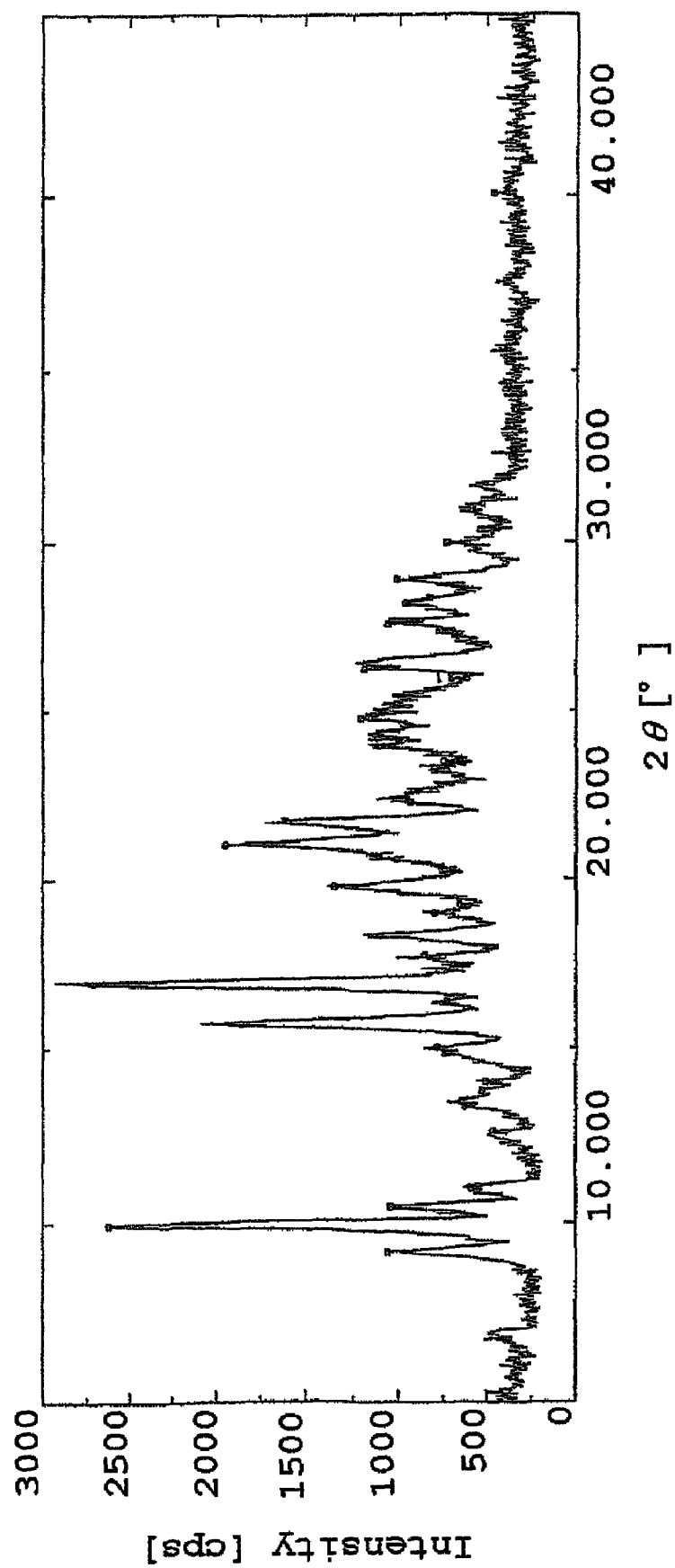
FIG. 20 shows a powder X-ray diffraction chart of the crystal of Example 17.

As a result of the powder X-ray diffraction analysis of this crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 20.

Example 18

The wet crystal (3.00 g) obtained in the above-mentioned Reference Example 3 was suspended in acetonitrile (10 mL) and water (40 mL) was added dropwise. After stirring for 6 hr, the precipitated crystal was separated.

Figure 21:
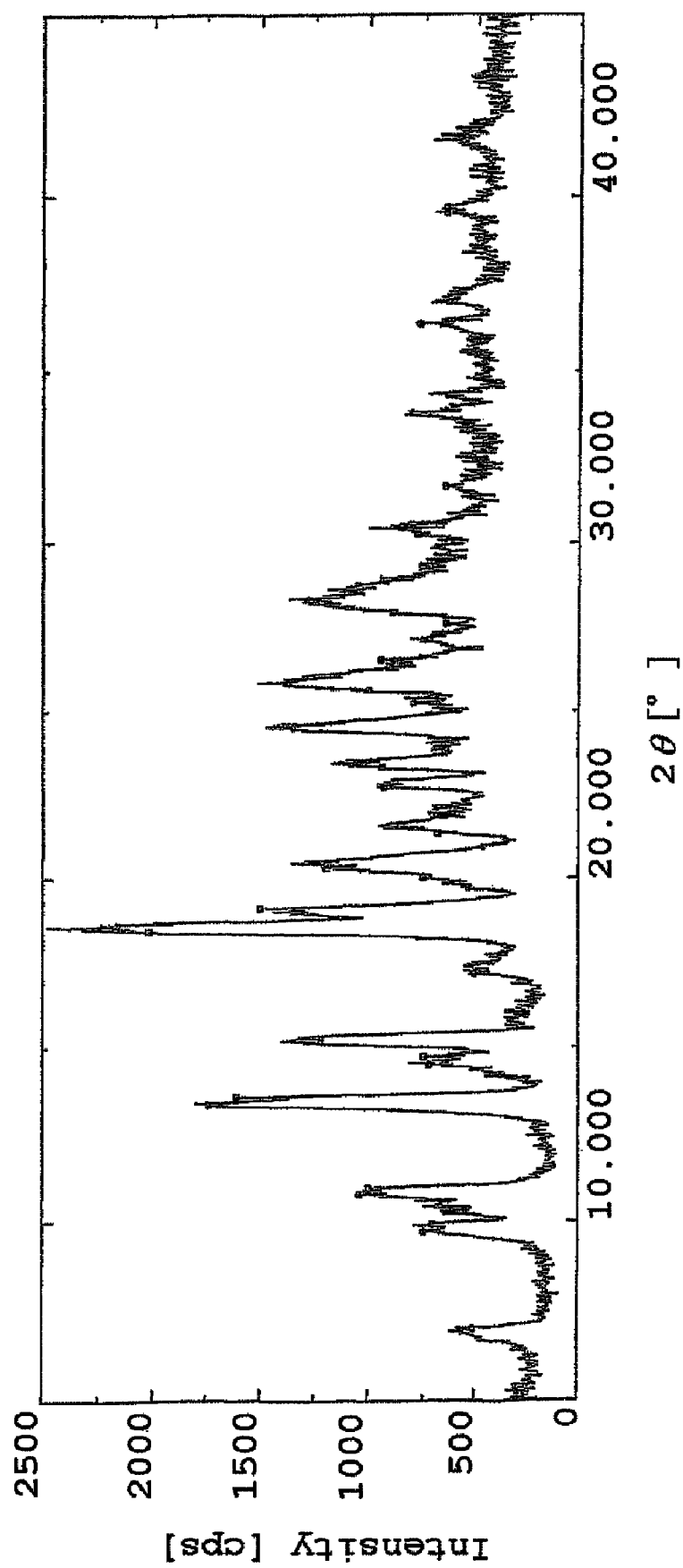
FIG. 21 shows a powder X-ray diffraction chart of the wet crystal of Example 18.

As a result of the powder X-ray diffraction analysis of this wet crystal, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 21.

As a result of the analysis of this wet crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 100% ee.

As a result of the analysis of the wet crystal by high performance liquid chromatography (condition (B)), 0.80% of a sulfide form and 0.33% of a sulfone form were present as analogous substances in the crystal, and other analogous substances were not present.

Example 19

The wet crystal obtained in the above-mentioned Example 18 was dried.

Figure 22:
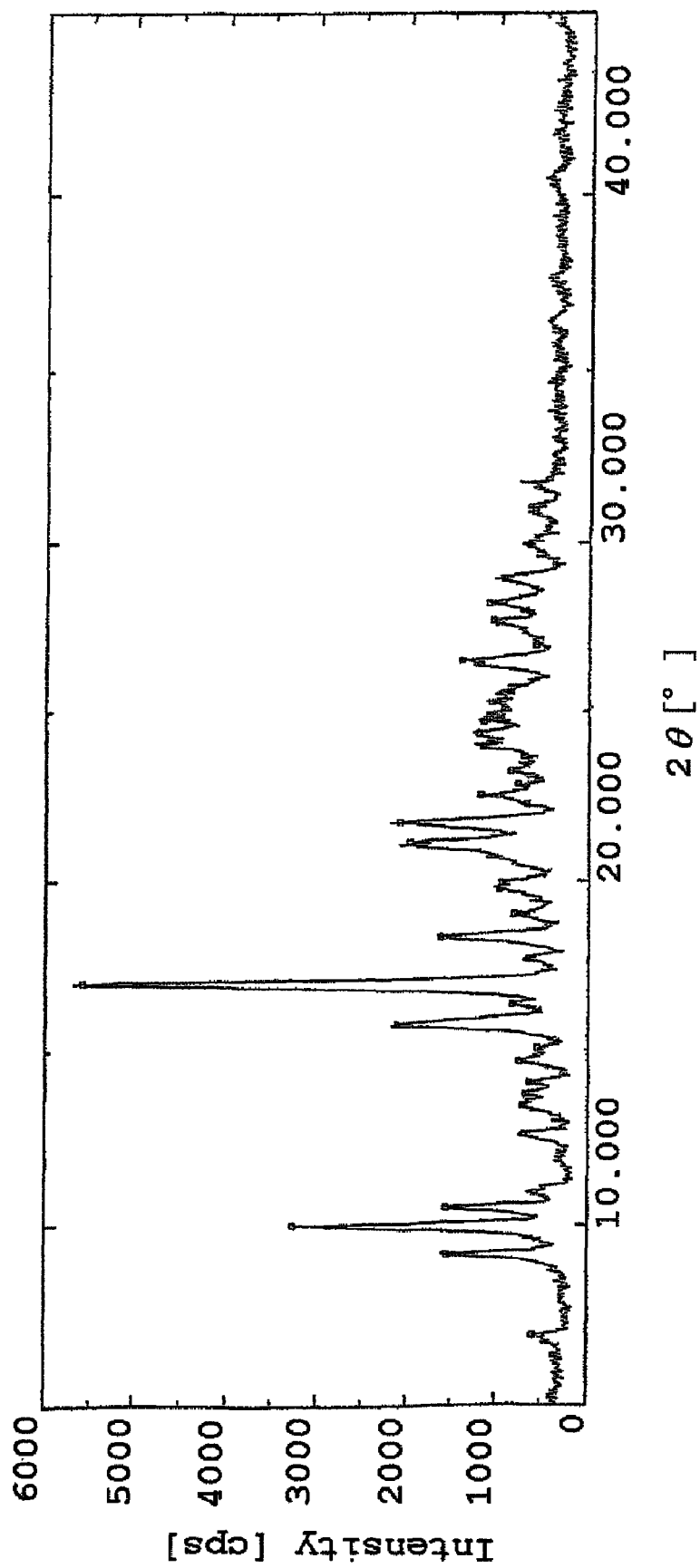
FIG. 22 shows a powder X-ray diffraction chart of the crystal of Example 19.

As a result of the powder X-ray diffraction analysis of this crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 22.

Example 20

The wet crystal (3.00 g) obtained in the above-mentioned Reference Example 3 was suspended in dimethyl sulfoxide (10 mL) and water (40 mL) was added dropwise. After stirring for 7 hr, the precipitated crystal was separated.

Figure 23:
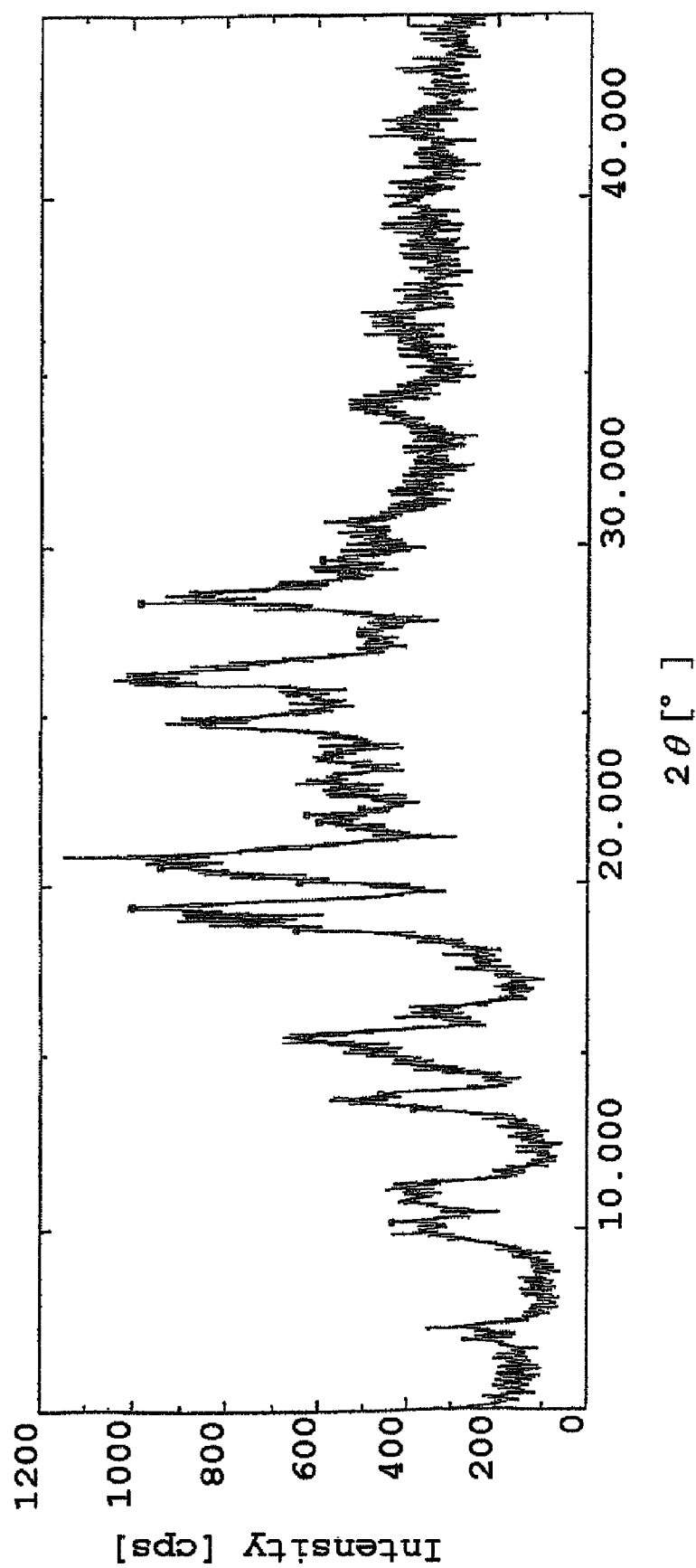
FIG. 23 shows a powder X-ray diffraction chart of the wet crystal of Example 20.

As a result of the powder X-ray diffraction analysis of this wet crystal, this wet crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 23.

As a result of the analysis of this wet crystal by high performance liquid chromatography (condition (A)), the enantiomer excess of (R)-2-[[[3-methyl-4-(2,2,2-trifluoroethoxy)-2-pyridyl]methyl]sulfinyl]benzimidazole in the crystal was 99.6% ee.

As a result of the analysis of the wet crystal by high performance liquid chromatography (condition (B)), 0.79% of a sulfide form and 0.37% of a sulfone form were present as analogous substances in the crystal, and other analogous substances were not present.

Example 21

The wet crystal obtained in the above-mentioned Example 20 was dried.

Figure 24:
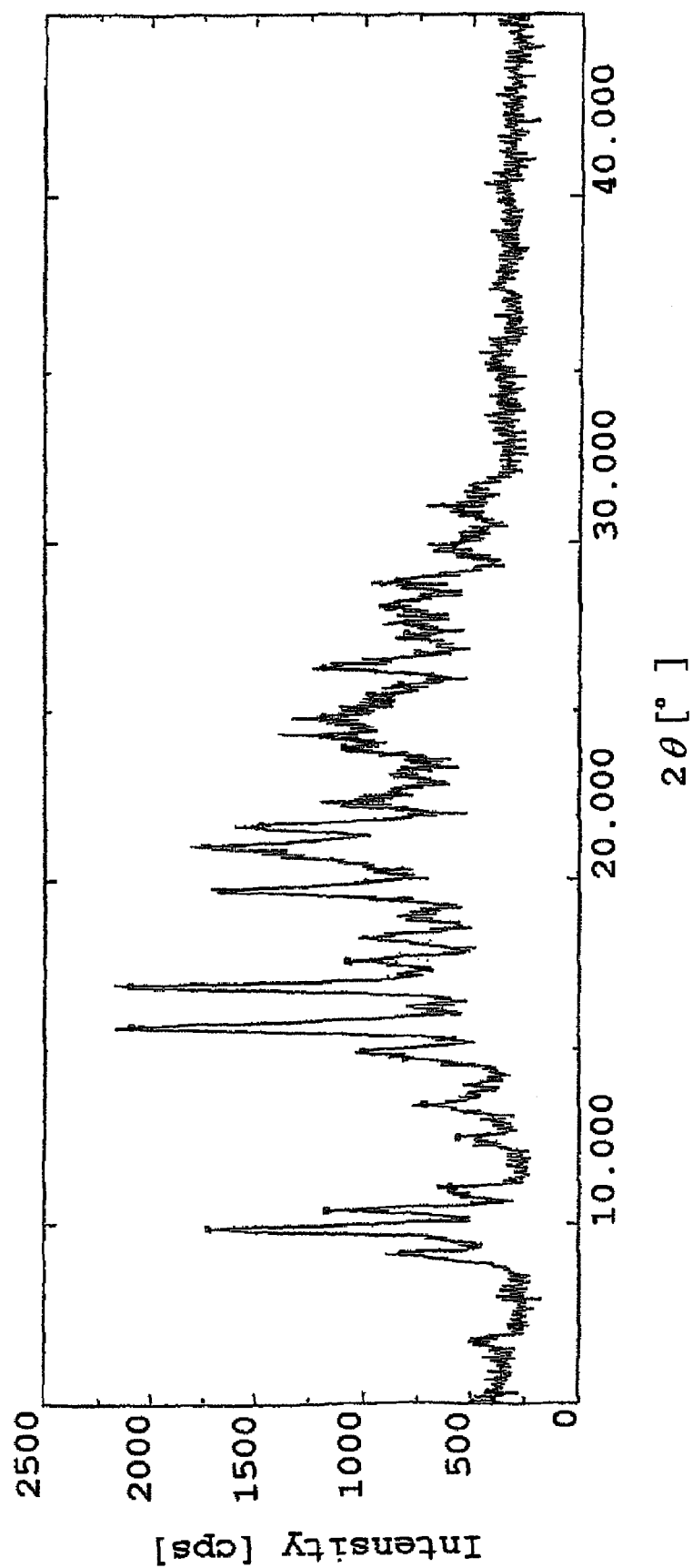
FIG. 24 shows a powder X-ray diffraction chart of the wet crystal of Example 21.

As a result of the powder X-ray diffraction analysis of this crystal, this crystal showed a powder X-ray diffraction pattern having characteristic peaks at interplanar spacings (d) of 8.33, 6.63, 5.86 and 4.82 Angstroms in powder X-ray diffraction. A chart of the powder X-ray diffraction is shown in FIG. 24.

Industrial Applicability

According to the production method of the present invention, a sulfone form difficult to remove, which is contained in an (R)-form or a salt thereof or an (S)-form or a salt thereof, can be removed easily, and a crystal of an (R)-form or a salt thereof or an (S)-form or a salt thereof having an extremely high enantiomer excess can be produced efficiently at an industrial large scale in high yield by a convenient method.

What is claimed is:
1. A crystal of (R)-2-[[[3-methyl-4-(2,2,2-trifluoroethoxy)-2-pyridyl]methyl]sulfinyl]benzimidazole.nH$_2$O (wherein n is about 0.1 to about 1.0) or a salt thereof.

* * * * *

UNITED STATES PATENT AND TRADEMARK OFFICE
CERTIFICATE OF CORRECTION

PATENT NO. : 8,212,046 B2
APPLICATION NO. : 13/168121
DATED : July 3, 2012
INVENTOR(S) : Hashimoto et al.

It is certified that error appears in the above-identified patent and that said Letters Patent is hereby corrected as shown below:

Specification, column 13, line 59: delete "(fee)" and insert --(%ee)--.

Signed and Sealed this
Fourteenth Day of May, 2013

Teresa Stanek Rea
*Acting Director of the United States Patent and Trademark Office*